United States Patent
Nguyen et al.

(10) Patent No.: US 9,950,075 B2
(45) Date of Patent: Apr. 24, 2018

(54) COMPOSITIONS AND METHODS FOR DELIVERING AGENTS TO THE CENTRAL NERVOUS SYSTEM

(71) Applicant: The University of Massachusetts, Boston, MA (US)

(72) Inventors: Son N. Nguyen, Amherst, MA (US); Cedric E. Bobst, Northampton, MA (US); Igor A. Kaltashov, Leverett, MA (US)

(73) Assignee: The University of Massachusetts, Boston, MA (US)

( * ) Notice: Subject to any disclaimer, the term of this patent is extended or adjusted under 35 U.S.C. 154(b) by 0 days.

(21) Appl. No.: 14/776,082

(22) PCT Filed: Mar. 14, 2014

(86) PCT No.: PCT/US2014/027607
§ 371 (c)(1),
(2) Date: Sep. 14, 2015

(87) PCT Pub. No.: WO2014/152678
PCT Pub. Date: Sep. 25, 2014

(65) Prior Publication Data
US 2017/0065720 A1    Mar. 9, 2017

Related U.S. Application Data

(60) Provisional application No. 61/798,764, filed on Mar. 15, 2013.

(51) Int. Cl.
| | |
|---|---|
| *A61K 38/54* | (2006.01) |
| *A61K 47/48* | (2006.01) |
| *C07K 14/79* | (2006.01) |
| *C12N 9/36* | (2006.01) |
| *A61K 38/47* | (2006.01) |
| *C12N 9/96* | (2006.01) |
| *A61K 47/64* | (2017.01) |

(52) U.S. Cl.
CPC ............ *A61K 47/483* (2013.01); *A61K 38/47* (2013.01); *A61K 47/644* (2017.08); *C07K 14/79* (2013.01); *C12N 9/2462* (2013.01); *C12N 9/96* (2013.01); *C12Y 302/01017* (2013.01); *C07K 2319/00* (2013.01)

(58) Field of Classification Search
None
See application file for complete search history.

(56) References Cited

U.S. PATENT DOCUMENTS

| | | | |
|---|---|---|---|
| 4,202,884 A | 5/1980 | Deconinck et al. | |
| 4,434,156 A | 2/1984 | Trowbridge | |
| 5,833,988 A | 11/1998 | Friden | |
| 5,993,809 A | 11/1999 | Weaver et al. | |
| 6,015,555 A | 1/2000 | Friden | |
| 6,099,835 A | 8/2000 | Kiczka | |
| 6,335,176 B1* | 1/2002 | Inglese | C07K 1/1072 |
| | | | 435/68.1 |
| 7,012,062 B2 | 3/2006 | Veronesi et al. | |
| 7,138,150 B2 | 11/2006 | Huang et al. | |
| 2002/0038010 A1* | 3/2002 | Hu | C12N 9/2462 |
| | | | 536/23.2 |
| 2008/0031868 A1 | 2/2008 | An | |
| 2010/0254899 A1* | 10/2010 | Capala | A61K 51/1045 |
| | | | 424/1.53 |

OTHER PUBLICATIONS

Gainey et al. J. Cell. Physiol. (1996) 168: 248-254.*
Sigma Catalog (1998) p. 702.*
Amet et al., Human growth hormone-transferrin fusion protein for oral delivery in hypophysectomized rats. J Control Release. Jan. 25, 2010;141(2):177-82. doi: 10.1016/j.jcorel.2009.09.007. Epub Sep. 15, 2009.
Begley, Delivery of therapeutic agents to the central nervous system: the problems and the possibilities. Pharmacol Ther. Oct. 2004;104(1):29-45.
Daniels et al., The transferrin receptor part II: targeted delivery of therapeutic agents into cancer cells. Clin Immunol. Nov. 2006;121(2):159-76. Epub Aug. 17, 2006.
Dennhart et al., Mass spectrometric real-time monitoring of enzymatic glycosidic hydrolysis, enzymatic inhibition and enzyme complexes. Anal Bioanal Chem. Oct. 2006;386(3):689-98. Epub Aug. 12, 2006.
Nguyen et al., Mass spectrometry-guided optimization and characterization of a biologically active transferrin-lysozyme model drug conjugate. Mol Pharm. May 6, 2013;10(5):1998-2007. doi: 10.1021/mp400026y. Epub Apr. 10, 2013.
Pardridge, Re-engineering biopharmaceuticals for delivery to brain with molecular Trojan horses. Bioconjug Chem. Jul. 2008;19(7):1327-38. doi:10.1021/bc800148t. Epub Jun. 12, 2008.
Pavan et al., Progress in drug delivery to the central nervous system by the prodrug approach. Molecules. May 1, 2008;13(5):1035-65.
Peppard et al., Pharmacologic options for CNS infections caused by resistant Gram-positive organisms. Expert Rev Anti Infect Ther. Feb. 2008;6(1):83-99. doi: 10.1586/14787210.6.1.83.
Shugar, The measurement of lysozyme activity and the ultra-violet inactivation of lysozyme. Biochim Biophys Acta. Mar. 1952;8(3):302-9.
Witt et al., Peptide drug modifications to enhance bioavailability and blood-brain barrier permeability. Peptides. Dec. 2001;22(12):2329-43.

* cited by examiner

*Primary Examiner* — Susan M Hanley
(74) *Attorney, Agent, or Firm* — Wolf, Greenfield & Sacks, P.C.

(57) ABSTRACT

The invention in some aspects provides compounds useful for targeting bacterial infections. In some embodiments, the compounds comprise a transferrin receptor ligand covalently linked to a bactericidal agent. In some embodiments, the bactericidal agent is a bactericidal peptide, such as a glycoside hydrolase (e.g., lysozyme).

19 Claims, 24 Drawing Sheets

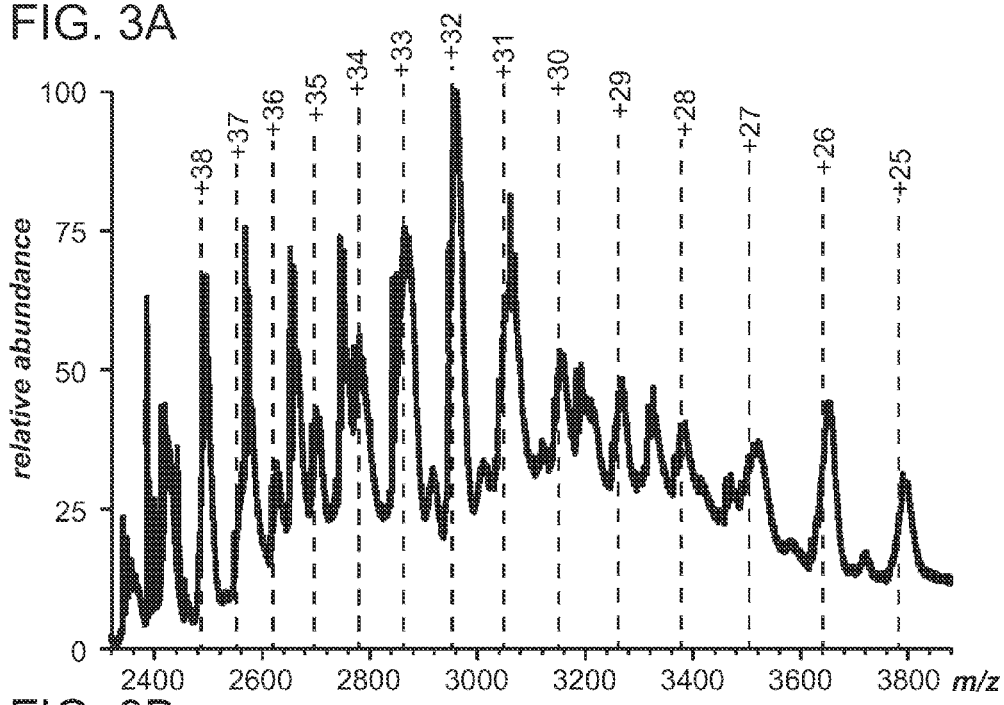
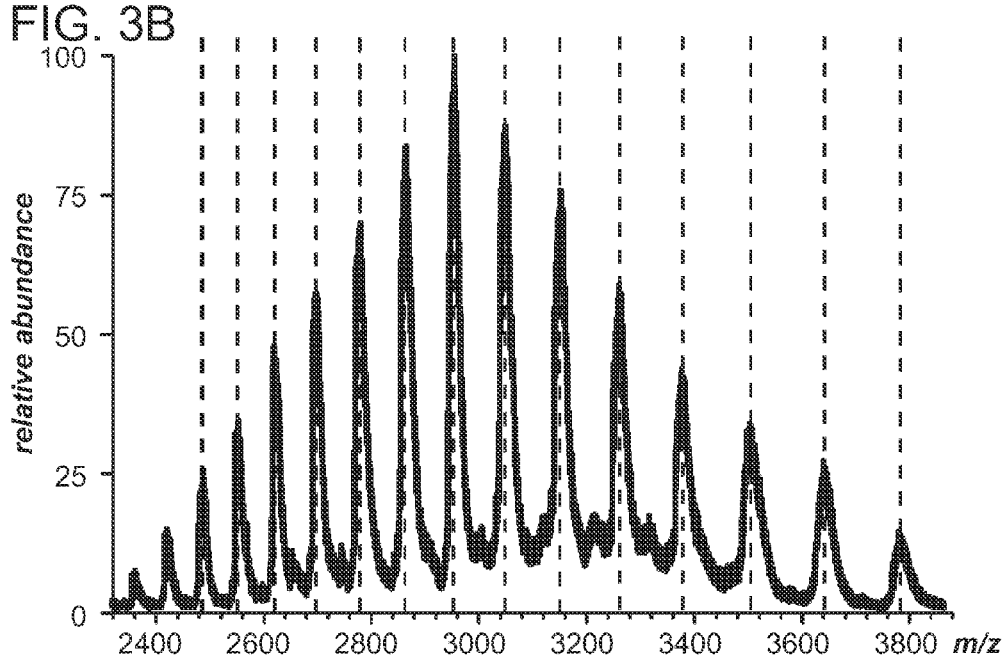

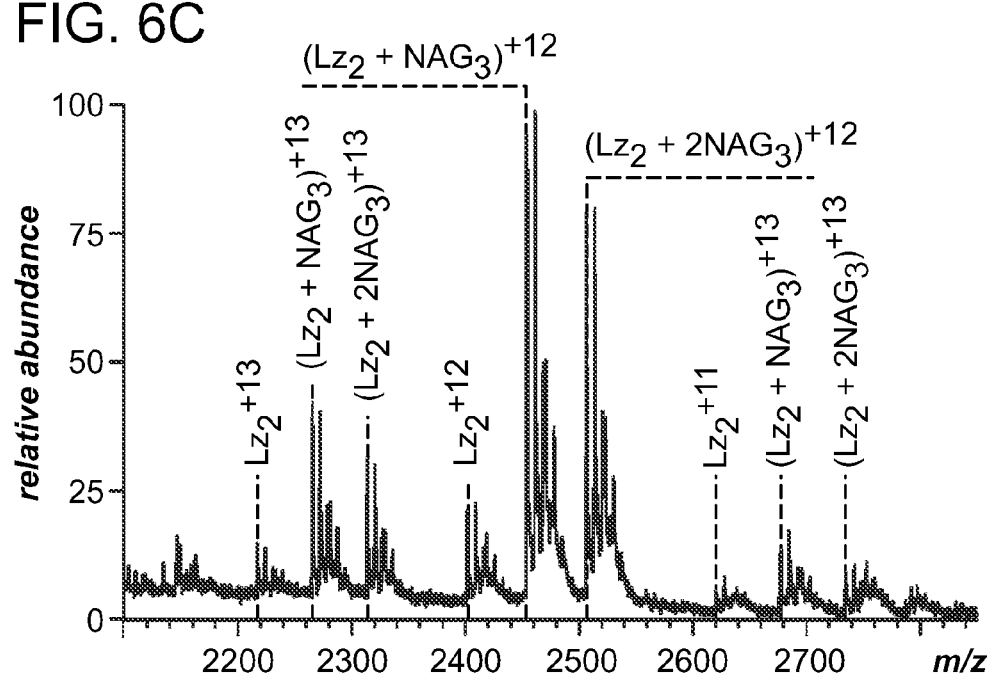
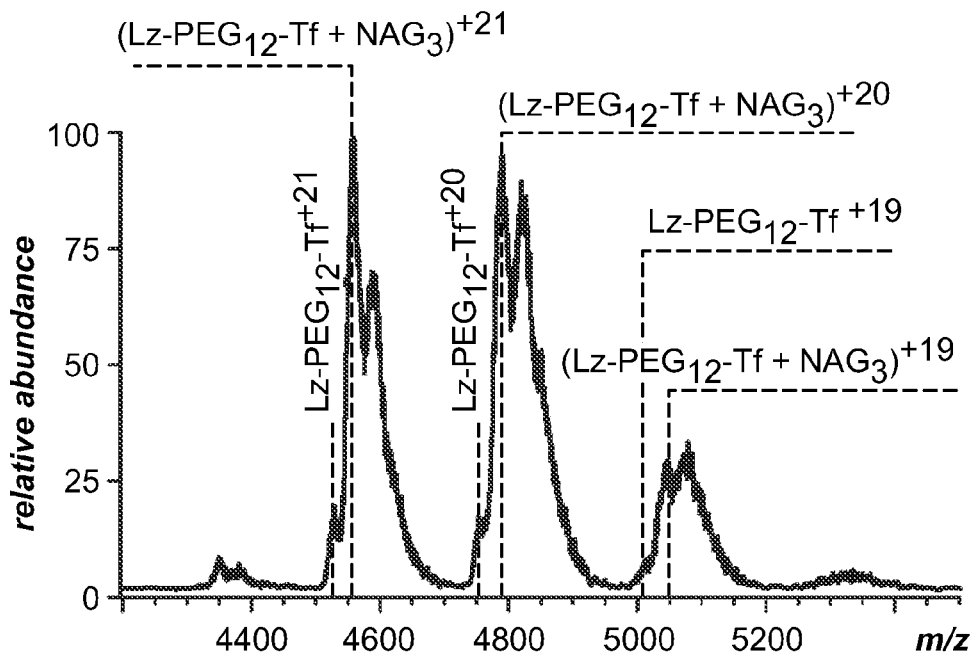

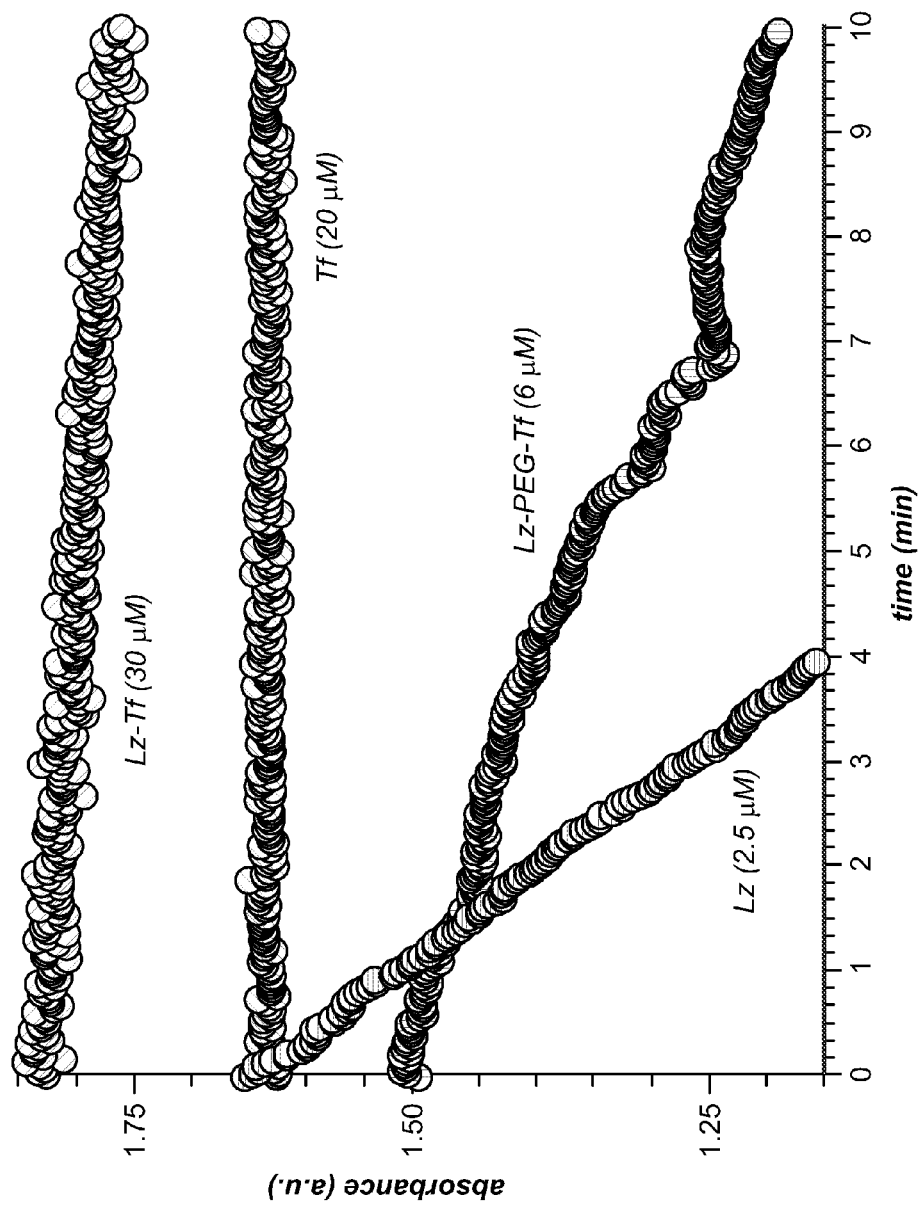

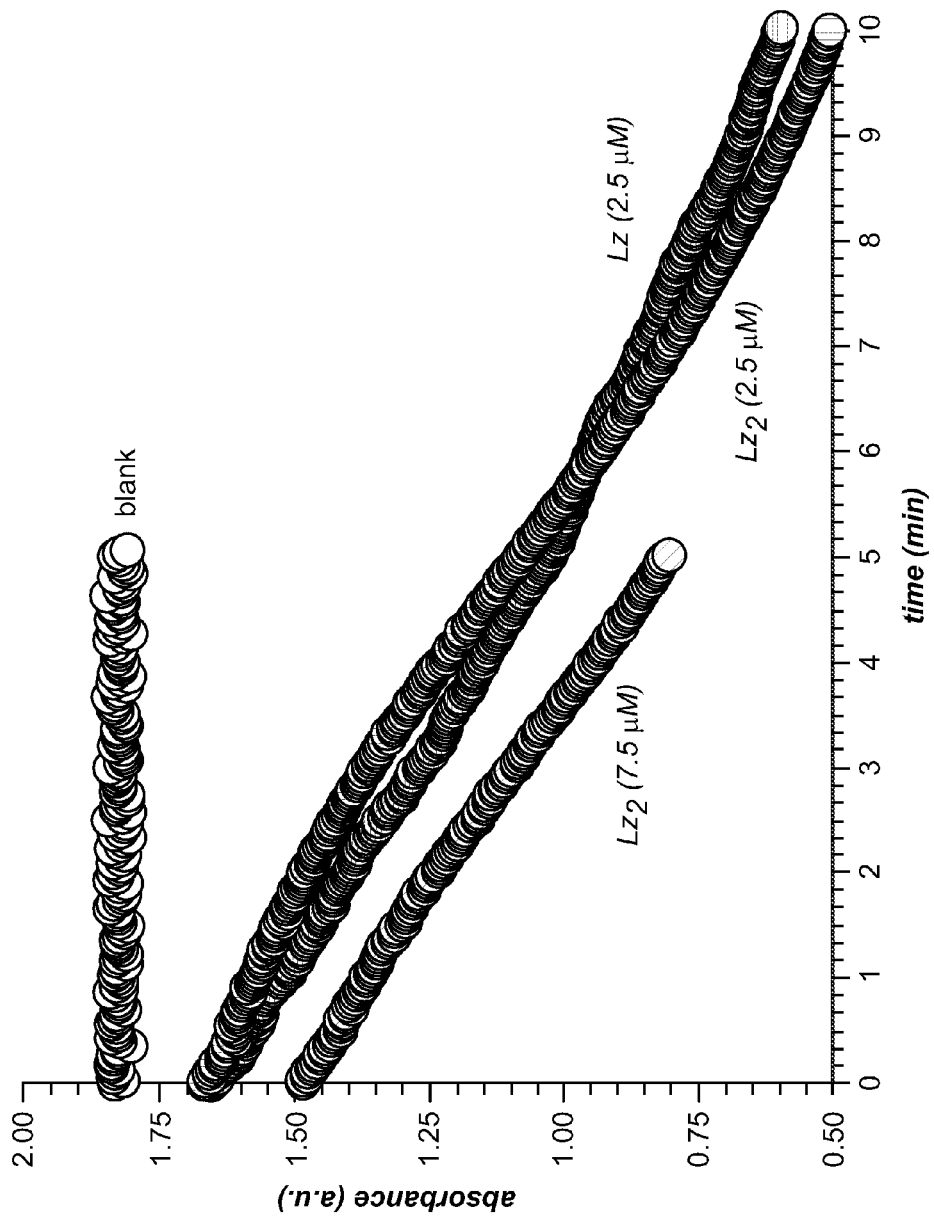

FIG. 8A

| | | | | | |
|---|---|---|---|---|---|
| 1 KVFGR | 6 CELAA | 11 AMKRH | 16 GLDNY | 21 RGYSL | 26 GNWVC | 31 AAKFE |
| 36 SNFNT | 41 QATNR | 46 NTDGS | 51 TDYGI | 56 LQINS | 61 RWWCN | 66 DGRTP |
| 71 GSRNL | 76 CNIPC | 81 SALLS | 86 SDITA | 91 SVNCA | 96 KKIVS | 101 DGNGM |
| 106 NAWVA | 111 WRNRC | 116 KGTDV | 121 QAWIR | 126 GCRL | | |

SEQ ID NO: 3

| | | | | |
|---|---|---|---|---|
| 1 VPDKTVRWCA | 11 VSEHEATKCQ | 21 SFRDHMKSVI | 31 PSDGPSVACV | 41 KKASYLDCIR | 51 AIAANEADAV |
| 61 TLDAGLVVDA | 71 YLAPNNLKPV | 81 VAEFYGSKED | 91 PQTFYYAVAV | 101 VKKDSGFQMN | 111 QLRGKKSCHT |
| 121 GLGRSAGWNI | 131 PIGLLYCDLP | 141 EPRKPLEKAV | 151 ANFFSGSCAP | 161 CADGTDFPQL | 171 CQLCPGCGCS |
| 181 TLNQYFGYSG | 191 AFKCLKDGAG | 201 DVAFVKHSTI | 211 FENLANKADR | 221 DQYELLCLDN | 231 TRKPVDEYKD |
| 241 CHLAQVPSHT | 251 VVARSMGGKE | 261 DLIWELLNQA | 271 QEHFGKDKSK | 281 EFQLFSSPHG | 291 KDLLFKDSAH |
| 301 GFLKVPPRMD | 311 AKMYLGYEYV | 321 TAIRNLREGT | 331 CPEAPTDECK | 341 PVKWCALSHH | 351 ERLKCDEWSV |
| 361 NSVGKIECVS | 371 AETTEDCIAK | 381 IMNGEADAMS | 391 LDGGFVYIAG | 401 KCGLVPVLAE | 411 NYNKSDNCED |
| 421 TPEAGYFAVA | 431 VVKKSASDLT | 441 WDNLKGKKSC | 451 HTAVGRTAGW | 461 NIPMGLLYNK | 471 INHCRFDEFF |
| 481 SEGCAPGSKK | 491 DSSLCKLCMG | 501 SGLNLCEPNN | 511 KEGYYGYTGA | 521 FRCLVEKGDV | 531 AFVKHQTVPQ |
| 541 NTGGKNPDPW | 551 AKNLNEKDYE | 561 LLCLDGTRKP | 571 VEEYANCHLA | 581 RAPNHAVVTR | 591 KDKEACVHKI |
| 601 LRQQQHLFGS | 611 NVTDCSGNFC | 621 LFRSETKDLL | 631 FRDDTVCLAK | 641 LHDRNTYEKY | 651 LGEEYVKAVG |
| 661 NLRKCSTSSL | 671 LEACTFRRP | SEQ ID NO: 4 | | | |

FIG. 8B

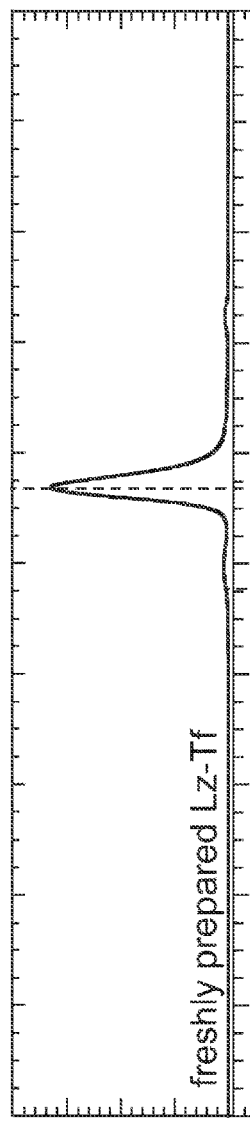
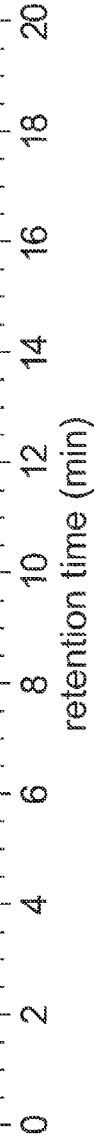
FIG. 12A
FIG. 12B
FIG. 12C
FIG. 12D

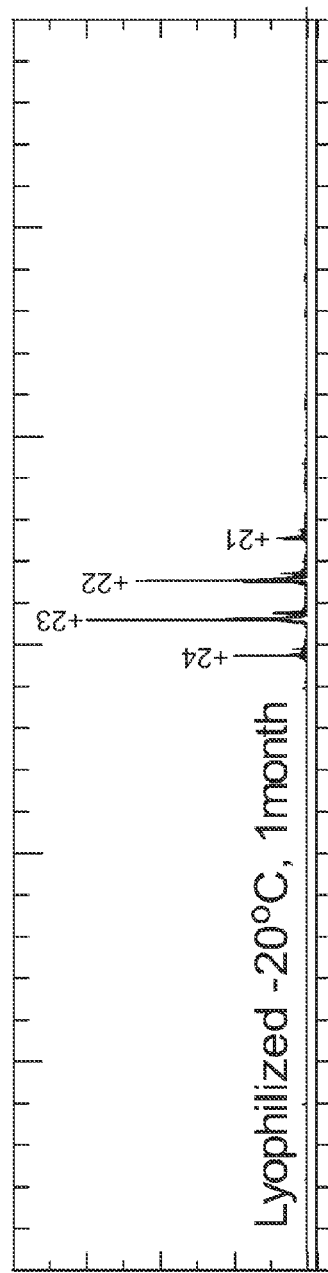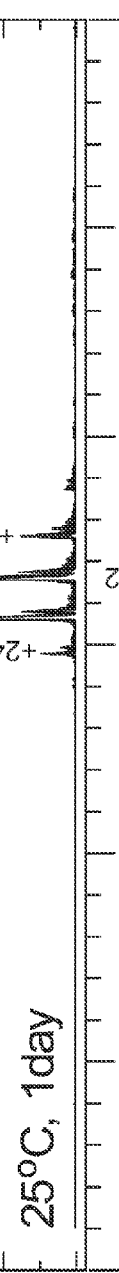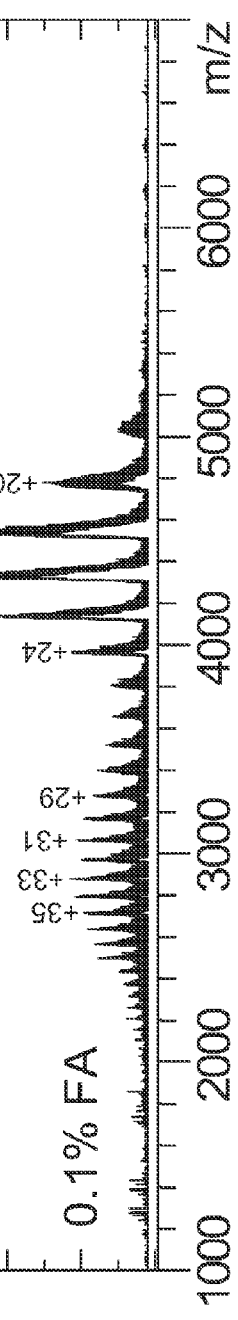

SEQUENCE LISTING

<160> NUMBER OF SEQ ID NOS: 6

<210> SEQ ID NO 1
<211> LENGTH: 698
<212> TYPE: PRT
<213> ORGANISM: Homo sapiens

<400> SEQUENCE: 1

```
Met Arg Leu Ala Val Gly Ala Leu Leu Val Cys Ala Val Leu Gly Leu
1               5                   10                  15

Cys Leu Ala Val Pro Asp Lys Thr Val Arg Trp Cys Ala Val Ser Glu
            20                  25                  30

His Glu Ala Thr Lys Cys Gln Ser Phe Arg Asp His Met Lys Ser Val
        35                  40                  45

Ile Pro Ser Asp Gly Pro Ser Val Ala Cys Val Lys Lys Ala Ser Tyr
    50                  55                  60

Leu Asp Cys Ile Arg Ala Ile Ala Ala Asn Glu Ala Asp Ala Val Thr
65                  70                  75                  80

Leu Asp Ala Gly Leu Val Tyr Asp Ala Tyr Leu Ala Pro Asn Asn Leu
                85                  90                  95

Lys Pro Val Val Ala Glu Phe Tyr Gly Ser Lys Glu Asp Pro Gln Thr
            100                 105                 110

Phe Tyr Tyr Ala Val Ala Val Val Lys Lys Asp Ser Gly Phe Gln Met
        115                 120                 125

Asn Gln Leu Arg Gly Lys Lys Ser Cys His Thr Gly Leu Gly Arg Ser
    130                 135                 140

Ala Gly Trp Asn Ile Pro Ile Gly Leu Leu Tyr Cys Asp Leu Pro Glu
145                 150                 155                 160

Pro Arg Lys Pro Leu Glu Lys Ala Val Ala Asn Phe Phe Ser Gly Ser
                165                 170                 175

Cys Ala Pro Cys Ala Asp Gly Thr Asp Phe Pro Gln Leu Cys Gln Leu
            180                 185                 190

Cys Pro Gly Cys Gly Cys Ser Thr Leu Asn Gln Tyr Phe Gly Tyr Ser
        195                 200                 205

Gly Ala Phe Lys Cys Leu Lys Asp Gly Ala Gly Asp Val Ala Phe Val
    210                 215                 220

Lys His Ser Thr Ile Phe Glu Asn Leu Ala Asn Lys Ala Asp Arg Asp
225                 230                 235                 240

Gln Tyr Glu Leu Leu Cys Leu Asp Asn Thr Arg Lys Pro Val Asp Glu
                245                 250                 255

Tyr Lys Asp Cys His Leu Ala Gln Val Pro Ser His Thr Val Val Ala
            260                 265                 270

Arg Ser Met Gly Gly Lys Glu Asp Leu Ile Trp Glu Leu Leu Asn Gln
        275                 280                 285

Ala Gln Glu His Phe Gly Lys Asp Lys Ser Lys Glu Phe Gln Leu Phe
    290                 295                 300

Ser Ser Pro His Gly Lys Asp Leu Leu Phe Lys Asp Ser Ala His Gly
305                 310                 315                 320

Phe Leu Lys Val Pro Pro Arg Met Asp Ala Lys Met Tyr Leu Gly Tyr
                325                 330                 335

Glu Tyr Val Thr Ala Ile Arg Asn Leu Arg Glu Gly Thr Cys Pro Glu
            340                 345                 350

Ala Pro Thr Asp Glu Cys Lys Pro Val Lys Trp Cys Ala Leu Ser His
        355                 360                 365
```

```
His Glu Arg Leu Lys Cys Asp Glu Trp Ser Val Asn Ser Val Gly Lys
    370                 375                 380

Ile Glu Cys Val Ser Ala Glu Thr Thr Glu Asp Cys Ile Ala Lys Ile
385                 390                 395                 400

Met Asn Gly Glu Ala Asp Ala Met Ser Leu Asp Gly Gly Phe Val Tyr
                405                 410                 415

Ile Ala Gly Lys Cys Gly Leu Val Pro Val Leu Ala Glu Asn Tyr Asn
                420                 425                 430

Lys Ser Asp Asn Cys Glu Asp Thr Pro Glu Ala Gly Tyr Phe Ala Val
                435                 440                 445

Ala Val Val Lys Lys Ser Ala Ser Asp Leu Thr Trp Asp Asn Leu Lys
    450                 455                 460

Gly Lys Lys Ser Cys His Thr Ala Val Gly Arg Thr Ala Gly Trp Asn
465                 470                 475                 480

Ile Pro Met Gly Leu Leu Tyr Asn Lys Ile Asn His Cys Arg Phe Asp
                485                 490                 495

Glu Phe Phe Ser Glu Gly Cys Ala Pro Gly Ser Lys Lys Asp Ser Ser
                500                 505                 510

Leu Cys Lys Leu Cys Met Gly Ser Gly Leu Asn Leu Cys Glu Pro Asn
    515                 520                 525

Asn Lys Glu Gly Tyr Tyr Gly Tyr Thr Gly Ala Phe Arg Cys Leu Val
    530                 535                 540

Glu Lys Gly Asp Val Ala Phe Val Lys His Gln Thr Val Pro Gln Asn
545                 550                 555                 560

Thr Gly Gly Lys Asn Pro Asp Pro Trp Ala Lys Asn Leu Asn Glu Lys
                565                 570                 575

Asp Tyr Glu Leu Leu Cys Leu Asp Gly Thr Arg Lys Pro Val Glu Glu
                580                 585                 590

Tyr Ala Asn Cys His Leu Ala Arg Ala Pro Asn His Ala Val Val Thr
                595                 600                 605

Arg Lys Asp Lys Glu Ala Cys Val His Lys Ile Leu Arg Gln Gln Gln
    610                 615                 620

His Leu Phe Gly Ser Asn Val Thr Asp Cys Ser Gly Asn Phe Cys Leu
625                 630                 635                 640

Phe Arg Ser Glu Thr Lys Asp Leu Leu Phe Arg Asp Asp Thr Val Cys
                645                 650                 655

Leu Ala Lys Leu His Asp Arg Asn Thr Tyr Glu Lys Tyr Leu Gly Glu
                660                 665                 670

Glu Tyr Val Lys Ala Val Gly Asn Leu Arg Lys Cys Ser Thr Ser Ser
                675                 680                 685

Leu Leu Glu Ala Cys Thr Phe Arg Arg Pro
    690                 695

<210> SEQ ID NO 2
<211> LENGTH: 146
<212> TYPE: PRT
<213> ORGANISM: Gallus gallus domesticus

<400> SEQUENCE: 2

Arg Ser Leu Leu Ile Leu Val Leu Cys Phe Leu Pro Leu Ala Ala Leu
1               5                   10                  15

Gly Lys Val Phe Gly Arg Cys Glu Leu Ala Ala Ala Met Lys Arg His
                20                  25                  30

Gly Leu Asp Asn Tyr Arg Gly Tyr Ser Leu Gly Asn Trp Val Cys Ala
                35                  40                  45
```

-continued

```
Ala Lys Phe Glu Ser Asn Phe Asn Thr Gln Ala Thr Asn Arg Asn Thr
 50                  55                  60

Asp Gly Ser Thr Asp Tyr Gly Ile Leu Gln Ile Asn Ser Arg Trp Trp
 65                  70                  75                  80

Cys Asn Asp Gly Arg Thr Pro Gly Ser Arg Asn Leu Cys Asn Ile Pro
                 85                  90                  95

Cys Ser Ala Leu Leu Ser Ser Asp Ile Thr Ala Ser Val Asn Cys Ala
            100                 105                 110

Lys Lys Ile Val Ser Asp Gly Asn Gly Met Asn Ala Trp Val Ala Trp
        115                 120                 125

Arg Asn Arg Cys Lys Gly Thr Asp Val Gln Ala Trp Ile Arg Gly Cys
130                 135                 140

Arg Leu
145

<210> SEQ ID NO 3
<211> LENGTH: 130
<212> TYPE: PRT
<213> ORGANISM: Gallus gallus domesticus

<400> SEQUENCE: 3

Met Lys Val Phe Gly Arg Cys Glu Leu Ala Ala Ala Met Lys Arg His
  1               5                  10                  15

Gly Leu Asp Asn Tyr Arg Gly Tyr Ser Leu Gly Asn Trp Val Cys Ala
             20                  25                  30

Ala Lys Phe Glu Ser Asn Phe Asn Thr Gln Ala Thr Asn Arg Asn Thr
         35                  40                  45

Asp Gly Ser Thr Asp Tyr Gly Ile Leu Gln Ile Asn Ser Arg Trp Trp
 50                  55                  60

Cys Asn Asp Gly Arg Thr Pro Gly Ser Arg Asn Leu Cys Asn Ile Pro
 65                  70                  75                  80

Cys Ser Ala Leu Leu Ser Ser Asp Ile Thr Ala Ser Val Asn Cys Ala
                 85                  90                  95

Lys Lys Ile Val Ser Asp Gly Asn Gly Met Asn Ala Trp Val Ala Trp
            100                 105                 110

Arg Asn Arg Cys Lys Gly Thr Asp Val Gln Ala Trp Ile Arg Gly Cys
        115                 120                 125

Arg Leu
    130

<210> SEQ ID NO 4
<211> LENGTH: 679
<212> TYPE: PRT
<213> ORGANISM: Homo sapiens

<400> SEQUENCE: 4

Val Pro Asp Lys Thr Val Arg Trp Cys Ala Val Ser Glu His Glu Ala
  1               5                  10                  15

Thr Lys Cys Gln Ser Phe Arg Asp His Met Lys Ser Val Ile Pro Ser
             20                  25                  30

Asp Gly Pro Ser Val Ala Cys Val Lys Lys Ala Ser Tyr Leu Asp Cys
         35                  40                  45

Ile Arg Ala Ile Ala Ala Asn Glu Ala Asp Ala Val Thr Leu Asp Ala
 50                  55                  60

Gly Leu Val Tyr Asp Ala Tyr Leu Ala Pro Asn Asn Leu Lys Pro Val
 65                  70                  75                  80
```

```
Val Ala Glu Phe Tyr Gly Ser Lys Glu Asp Pro Gln Thr Phe Tyr Tyr
                85                  90                  95

Ala Val Ala Val Val Lys Lys Asp Ser Gly Phe Gln Met Asn Gln Leu
            100                 105                 110

Arg Gly Lys Lys Ser Cys His Thr Gly Leu Gly Arg Ser Ala Gly Trp
            115                 120                 125

Asn Ile Pro Ile Gly Leu Leu Tyr Cys Asp Leu Pro Glu Pro Arg Lys
        130                 135                 140

Pro Leu Glu Lys Ala Val Ala Asn Phe Phe Ser Gly Ser Cys Ala Pro
145                 150                 155                 160

Cys Ala Asp Gly Thr Asp Phe Pro Gln Leu Cys Gln Leu Cys Pro Gly
                165                 170                 175

Cys Gly Cys Ser Thr Leu Asn Gln Tyr Phe Gly Tyr Ser Gly Ala Phe
            180                 185                 190

Lys Cys Leu Lys Asp Gly Ala Gly Asp Val Ala Phe Val Lys His Ser
        195                 200                 205

Thr Ile Phe Glu Asn Leu Ala Asn Lys Ala Asp Arg Asp Gln Tyr Glu
    210                 215                 220

Leu Leu Cys Leu Asp Asn Thr Arg Lys Pro Val Asp Glu Tyr Lys Asp
225                 230                 235                 240

Cys His Leu Ala Gln Val Pro Ser His Thr Val Val Ala Arg Ser Met
                245                 250                 255

Gly Gly Lys Glu Asp Leu Ile Trp Glu Leu Leu Asn Gln Ala Gln Glu
            260                 265                 270

His Phe Gly Lys Asp Lys Ser Lys Glu Phe Gln Leu Phe Ser Ser Pro
        275                 280                 285

His Gly Lys Asp Leu Leu Phe Lys Asp Ser Ala His Gly Phe Leu Lys
    290                 295                 300

Val Pro Pro Arg Met Asp Ala Lys Met Tyr Leu Gly Tyr Glu Tyr Val
305                 310                 315                 320

Thr Ala Ile Arg Asn Leu Arg Glu Gly Thr Cys Pro Glu Ala Pro Thr
                325                 330                 335

Asp Glu Cys Lys Pro Val Lys Trp Cys Ala Leu Ser His His Glu Arg
            340                 345                 350

Leu Lys Cys Asp Glu Trp Ser Val Asn Ser Val Gly Lys Ile Glu Cys
        355                 360                 365

Val Ser Ala Glu Thr Thr Glu Asp Cys Ile Ala Lys Ile Met Asn Gly
    370                 375                 380

Glu Ala Asp Ala Met Ser Leu Asp Gly Gly Phe Val Tyr Ile Ala Gly
385                 390                 395                 400

Lys Cys Gly Leu Val Pro Val Leu Ala Glu Asn Tyr Asn Lys Ser Asp
                405                 410                 415

Asn Cys Glu Asp Thr Pro Glu Ala Gly Tyr Phe Ala Val Ala Val Val
            420                 425                 430

Lys Lys Ser Ala Ser Asp Leu Thr Trp Asp Asn Leu Lys Gly Lys Lys
        435                 440                 445

Ser Cys His Thr Ala Val Gly Arg Thr Ala Gly Trp Asn Ile Pro Met
    450                 455                 460
```

```
Gly Leu Leu Tyr Asn Lys Ile Asn His Cys Arg Phe Asp Glu Phe Phe
465                 470                 475                 480

Ser Glu Gly Cys Ala Pro Gly Ser Lys Lys Asp Ser Ser Leu Cys Lys
                485                 490                 495

Leu Cys Met Gly Ser Gly Leu Asn Leu Cys Glu Pro Asn Asn Lys Glu
            500                 505                 510

Gly Tyr Tyr Gly Tyr Thr Gly Ala Phe Arg Cys Leu Val Glu Lys Gly
        515                 520                 525

Asp Val Ala Phe Val Lys His Gln Thr Val Pro Gln Asn Thr Gly Gly
    530                 535                 540

Lys Asn Pro Asp Pro Trp Ala Lys Asn Leu Asn Glu Lys Asp Tyr Glu
545                 550                 555                 560

Leu Leu Cys Leu Asp Gly Thr Arg Lys Pro Val Glu Glu Tyr Ala Asn
                565                 570                 575

Cys His Leu Ala Arg Ala Pro Asn His Ala Val Val Thr Arg Lys Asp
            580                 585                 590

Lys Glu Ala Cys Val His Lys Ile Leu Arg Gln Gln Gln His Leu Phe
        595                 600                 605

Gly Ser Asn Val Thr Asp Cys Ser Gly Asn Phe Cys Leu Phe Arg Ser
610                 615                 620

Glu Thr Lys Asp Leu Leu Phe Arg Asp Asp Thr Val Cys Leu Ala Lys
625                 630                 635                 640

Leu His Asp Arg Asn Thr Tyr Glu Lys Tyr Leu Gly Glu Tyr Val
                645                 650                 655

Lys Ala Val Gly Asn Leu Arg Lys Cys Ser Thr Ser Leu Leu Glu
        660                 665                 670

Ala Cys Thr Phe Arg Arg Pro
        675

<210> SEQ ID NO 5
<211> LENGTH: 19
<212> TYPE: PRT
<213> ORGANISM: Homo sapiens

<400> SEQUENCE: 5

Met Arg Leu Ala Val Gly Ala Leu Leu Val Cys Ala Val Leu Gly Leu
1               5                   10                  15

Cys Leu Ala

<210> SEQ ID NO 6
<211> LENGTH: 17
<212> TYPE: PRT
<213> ORGANISM: Gallus gallus domesticus

<400> SEQUENCE: 6

Arg Ser Leu Leu Ile Leu Val Leu Cys Phe Leu Pro Leu Ala Ala Leu
1               5                   10                  15

Gly
```

COMPOSITIONS AND METHODS FOR DELIVERING AGENTS TO THE CENTRAL NERVOUS SYSTEM

RELATED APPLICATIONS

This application is a national stage filing under U.S.C. § 371 of International Application PCT/US2014/027607, entitled "COMPOSITIONS AND METHODS FOR DELIVERING AGENTS TO THE CENTRAL NERVOUS SYSTEM" having an international filing date of Mar. 14, 2014, which claims the benefit under 35 U.S.C. § 119(e) of U.S. provisional application Ser. No. 61/798,764, entitled "COMPOSITIONS AND METHODS FOR DELIVERING AGENTS TO THE CENTRAL NERVOUS SYSTEM", filed Mar. 15, 2013, the entire contents of each application which are incorporated by reference herein.

FEDERALLY SPONSORED RESEARCH

This invention was made with government support under grant no. R01 GM061666 awarded by the National Institutes of Health, The government has certain rights in the invention.

BACKGROUND OF INVENTION

The incidence of CNS infections (brain infections) is rising at an alarming rate, while the treatment options remain very limited. Only a very small faction of existing small-molecule medicines can penetrate the BBB, and none of the currently approved protein therapeutics is capable of doing so. Coupled with the ever increasing resistance of pathogens to common antibiotics and dire side effects of the immune system's inflammation response to infection (frequently leading to brain abscess), this presents the clinicians with a grave challenge.

SUMMARY OF INVENTION

The invention in some aspects provides compounds useful for targeting bacterial infections. In some embodiments, the compounds comprise a transferrin receptor ligand covalently linked to a bactericidal agent. In some embodiments, the bactericidal agent is a bactericidal peptide, such as a glycoside hydrolase (e.g., lysozyme). In some embodiments, the compounds are useful for treating bacterial infections of the CNS through intravascular administration because the transferrin receptor ligand facilitates passage of the compound across the blood-brain-barrier and thus delivery of the bactericidal agent to the CNS.

According to some aspects of the invention compounds are provided that have the formula $X_1$-L-$X_2$, wherein L is a linker that covalently links $X_1$ to $X_2$, wherein $X_1$ is a transferrin receptor ligand, and $X_2$ is a glycoside hydrolase. In some embodiments, the transferrin receptor ligand is transferrin. In some embodiments, the transferrin is human transferrin. In some embodiments, the transferrin receptor ligand is an antibody or antigen-binding fragment that selectively binds to the transferrin receptor. In some embodiments, the glycoside hydrolase is a lysozyme. In some embodiments, the lysozyme is chicken or human lysozyme. In some embodiments, the glycoside hydrolase hydrolyzes the β-1,4-glycosidic bond between the N-acetylmuramic acid (NAM) and N-acetylglucosamine (NAG) residues of peptidoglycans. In some embodiments, the glycoside hydrolase hydrolyzes the 1,4-beta-linkages between N-acetyl-D-glucosamine residues in chitodextrins.

In some embodiments, the linker comprises a linear molecule comprising at least 10 rotatable bonds. In some embodiments, the linker comprises a linear molecule of at least 30 Å in length. In some embodiments, the linker comprises a molecule having a Polar Surface Area (PSA) to Total Surface Area (TSA) ratio of at least 55%, at least 65%, at least 75%, or at least 85%. In some embodiments, the linker comprises a molecule having one or more biodegradable segments.

In some embodiments the compound is of the formula:

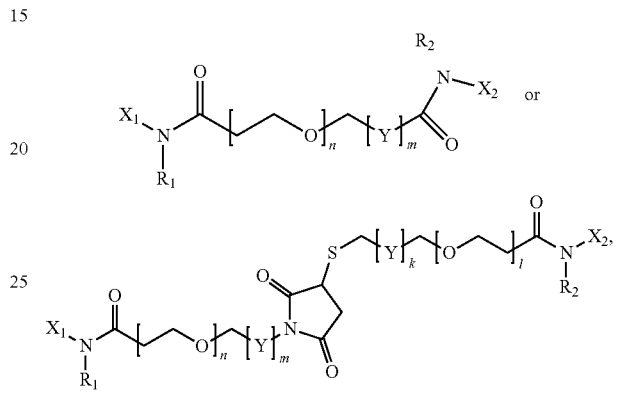

wherein n and l are each independently an integer from 1 to 100, wherein m and k are each independently an integer from 1 to 4, wherein each instance of Y is independently selected from the group consisting of —N($R_3$)C(=O)—, —C(=O)N($R_3$)—, and —C($R_4$)$_2$—, and wherein: $R_1$, $R_2$, and each instance of $R_3$ are independently selected from the group consisting of hydrogen, optionally substituted C1-6 alkyl, and a nitrogen protecting group; each instance of $R_4$ is independently selected from the group consisting of hydrogen, halogen, optionally unsubstituted acyl, optionally unsubstituted alkyl, optionally unsubstituted alkenyl, optionally unsubstituted alkynyl, optionally unsubstituted carbocyclyl, optionally unsubstituted heterocyclyl, optionally unsubstituted aryl, optionally unsubstituted heteroaryl, —OR$_A$, —N(R$_A$)2, —SR$_A$, —CN, —SCN, —C(=NR$_A$)R$_A$, —C(=NR$_A$)OR$_A$, —C(=NR$_A$)N(R$_A$)$_2$, —C(=O)R$_A$, —C(=O)OR$_A$, —C(=O)N(R$_A$)$_2$, —NO$_2$, —NR$_A$C(=O)R$_A$, —NR$_A$C(=O)OR$_A$, —NR$_A$C(=O)N(R$_A$)$_2$, —OC(=O)R$_A$, —OC(=O)OR$_A$, —OC(=O)N(R$_A$)$_2$, and a nitrogen protecting group when attached to a nitrogen atom, or two $R_4$ groups are joined to form an optionally unsubstituted carbocyclic, optionally unsubstituted heterocyclic, optionally unsubstituted aryl, or optionally unsubstituted heteroaryl ring; and each instance of $R_A$ is independently selected from the group consisting of hydrogen, optionally unsubstituted acyl, optionally unsubstituted alkyl, optionally unsubstituted alkenyl, optionally unsubstituted alkynyl, optionally unsubstituted carbocyclyl, optionally unsubstituted heterocyclyl, optionally unsubstituted aryl, optionally unsubstituted heteroaryl, a nitrogen protecting group when attached to a nitrogen atom, an oxygen protecting group when attached to an oxygen atom, and a sulfur protecting group when attached to a sulfur atom, or two $R_A$ groups are joined to form an optionally unsubstituted heterocyclic ring.

In some embodiments the compound is of the formula:

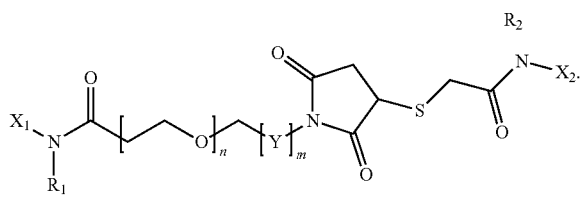

In some embodiments the compound is of the formula:

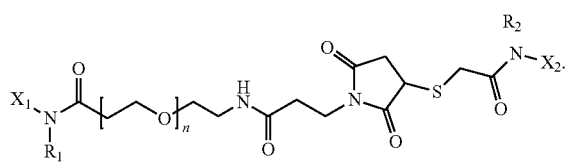

In some embodiments the compound is of the formula

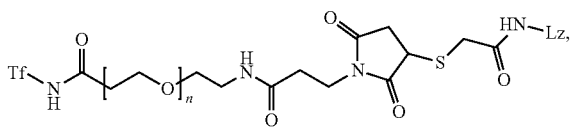

wherein Tf is transferrin and Lz is lysozyme.

In certain embodiments of the compounds, n is in the range of 4-24, 6-18, 8-16, or 10-14. In certain embodiments, n is 12. In some embodiments, $X_1$ is transferrin and the linker, L, is covalently linked to the transferrin at its N-terminal α-amino group or at the ε-amino group of its lysine at amino acid position 4, 144, 196 or 280, through an amide bond. In some embodiments, $X_1$ is transferrin and the linker, L, is covalently linked to the transferrin at the ε-amino group of its lysine at amino acid position 41, 42, 102, 103, 115, 116, 304, 591, 593, 599, 640, 664, through an amide bond. In some embodiments, $X_2$ is lysozyme and the linker, L, is covalently linked to the lysozyme at its N-terminal α-amino group or at the ε-amino group of its lysine at amino acid position 1, 13, 33, 96, 97, or 116, through an amide bond.

According to some aspects of the invention, multimeric compounds are provided that comprise a plurality of covalently linked monomers having the formula [$X_1$-L-$X_2$], wherein L is a linker that covalently links $X_1$ to $X_2$, wherein $X_1$ is a transferrin receptor ligand, and $X_2$ is a glycoside hydrolase.

According to some aspects of the invention, compositions are provided that comprise any one or more of the compounds disclosed herein and a carrier.

According to some aspects of the invention, compositions are provided that comprise a plurality of compounds, each of which compounds has a formula $X_1$-L-$X_2$, wherein L is a linker that covalently links $X_1$ to $X_2$, wherein $X_1$ is a transferrin receptor ligand, and $X_2$ is a glycoside hydrolase, wherein, for at least 50%, at least 60%, at least 70%, at least 80%, at least 90% or more of the compounds in the plurality, the linker, L, is covalently linked to transferrin at its N-terminal α-amino group and/or to the glycoside hydrolase at its N-terminal α-amino group.

According to some aspects of the invention, compositions are provided that comprise a mixture of compounds, wherein at least 50%, at least 60%, at least 70%, at least 80%, at least 90% or more of the compounds in the mixture are monomeric compounds having the formula $X_1$-L-$X_2$, wherein the remaining compounds comprise (i) multimeric compounds comprising a plurality of covalently linked monomers having the formula [$X_1$-L-$X_2$], and/or (ii) complexes of two or more covalently linked glycoside hydrolases, wherein L is a linker that covalently links $X_1$ to $X_2$, wherein $X_1$ is a transferrin receptor ligand, and $X_2$ is a glycoside hydrolase.

According to some aspects of the invention, pharmaceutical compositions are provided that comprise any one or more of the compounds disclosed herein and a pharmaceutically acceptable carrier.

According to some aspects of the invention, kits are provided that comprise a container housing any one or more of the compounds disclosed herein According to some aspects of the invention, methods of killing bacteria (e.g., gram-positive bacteria) are provided. In some embodiments, the methods involve contacting the bacteria with any one or more of the compounds or compositions disclosed herein in an amount effective to kill the bacteria (e.g., by breaking down the cell wall of the bacteria).

According to some aspects of the invention, methods of treating a bacterial infection of the central nervous system (CNS) in a subject are provided. In some embodiments, the methods involve administering to the CNS of the subject any one or more of the compounds or compositions disclosed herein in an amount effective for treating a bacterial infection in the CNS. In some embodiments, the step of administering comprises delivering the composition to the subject intravenously, wherein the compound enters the CNS by crossing the blood-brain-barrier. In some embodiments, the methods further comprise determining that the bacterial infection caused by a gram-positive bacteria, prior to administering the composition to the subject. In some embodiments, the methods further comprise obtaining a sample of CNS fluid from the subject and performing an assay to detect the presence of gram-positive bacteria in the CNS fluid. In some embodiments, the assay is a Gram stain assay or PCR assay.

In some embodiments, the bacteria comprise: Staphylococci, *Listeria monocytogenes, Staphylococcus aureus, Stayphylococcus epidermidis, Steptococcus pneumonia, Diphtheroid bacilli* or *Propionobacterium acnes*.

BRIEF DESCRIPTION OF DRAWINGS

FIGS. 2C and 2D show Tf and Lz activated with SM(PEG)12 and SATA, respectively. The series of peaks indicated with an asterisk represents salt adducts.

FIGS. 3A-3C. ESI mass spectra of crude (FIG. 3A) and IXC-purified (FIG. 3B) conjugation products of Lz and Tf. FIG. 3C shows IXC chromatogram of the crude mixture (the fraction whose mass spectrum is shown in FIG. 3B is highlighted in the chromatogram).

FIGS. 6A-6D. ESI mass spectra of NAG3/Lz (FIG. 6A), NAG3/Lz-Tf (FIG. 6B), NAG3/Lz2 (FIG. 6C) and NAG3/Lz-Tf longer linker (FIG. 6D) mixtures acquired under near-native conditions (5 µM of proteins and 10 µM NAG3 in 20 mM ammonium acetate, pH 7.1).

FIGS. 7A-7B. Antibacterial activity data for Lz-Tf conjugates compared to that of intact Lz and Tf (FIG. 7A) and Lz dimers (FIG. 7B).

FIG. 8A. Amino acid sequences of Lz with Lys residues highlighted.

FIG. 8B. Amino acid sequence of Tf with Lys residue highlighted.

FIGS. 12A-12D. SEC chromatogram of Lz-Tf conjugates acquired under conditions representing prolonged storage in lyophilized form (FIG. 12C) and post-administration (FIGS. 12B, 12D). Freshly prepared Lz-Tf (FIG. 12A) was the negative control to which the other samples were compared.

FIGS. 13A-13C. ESI mass spectra of Lz-Tf conjugates acquired after prolonged storage in lyophilized form (FIG. 13A) or after incubation at room temperature for 1 day (FIG. 13B). Lz-Tf conjugate denatured with 0.1% formic acid (FIG. 13C) represents a control sample and shows the high charge density ionic species associated with unfolded conjugate.

DETAILED DESCRIPTION OF INVENTION

Figure 1A:
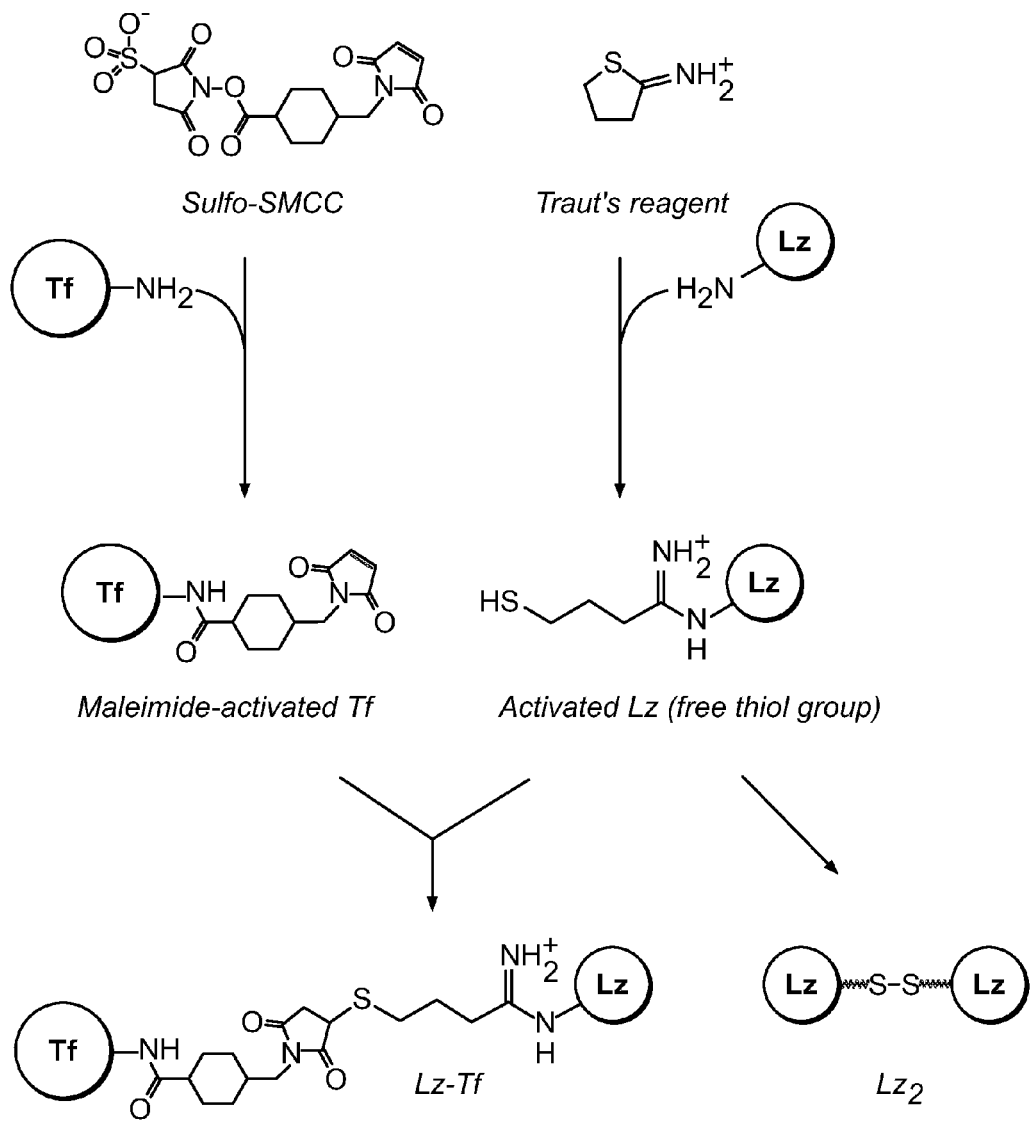
FIGS. 1A-1C. Schematic diagrams illustrating conjugation of Tf to Lz using the Traut's reagent and SMCC (FIG. 1A) and SATA and SM(PEG)12 (FIG. 1B), and possible side reactions due to excessive activation of the two proteins with the Traut's reagent and SMCC (FIG. 1C).

Some aspects of the invention are based on a recognition of an increasing number of bacterial pathogens resistant to common antibiotics. In some embodiments, Applicants have developed new antibiotic compounds based on bio-inspired host defense systems, such as amphiphilic peptides and other bacteriostatic macromolecules. In some embodiments, Applicants recognized that neuroanatomical obstacles may limit the effectiveness of antimicrobial therapeutics in the central nervous system (CNS) by preventing a large number of effective antimicrobials from reaching sufficient concentration levels at the infection site. Accordingly, in some embodiments, Applicants have developed compounds that are able to be delivered "on demand" across the Blood Brain Barrier (BBB). In some embodiments, the compounds employ a bactericidal agent designed to eradicate Gram-positive infections in the CNS, whose carriers gain access to the brain via a variety of routes.

In some embodiments, Applicants have developed compounds based on a group of enzymes that compromise the integrity of bacterial cell walls, as a class of bactericidal agents. In some embodiments, the compounds employ a glycoside hydrolase (e.g., Lysozyme). Lysozyme (Lz) is an antibacterial enzyme present in a variety of organisms that exerts its bacteriostatic function by hydrolyzing the β-1,4-glycosidic bond between the N-acetylmuramic acid (NAM) and N-acetylglucosamine (NAG) residues of peptidoglycans, resulting in lysis of the bacterial cell. Although Lz primarily attacks Gram-positive bacteria, where the peptidoglycan layer is not protected by the outer membrane (as it is in Gram-negative bacteria), certain structural modifications can make it effective against Gram-negative bacteria as well (such as by acylating with hydrophobic chains to enhance permeability to the cytoplasmic membrane of Gram-negative bacteria).

In some embodiments, Applicants have developed compounds comprising Lysozyme (Lz) conjugated to Transferrin (Tf) as a therapeutic that targets the CNS. Analytical protocols are established to characterize its structure and interactions with therapeutic targets and physiological partners influencing its successful delivery. Applicants demonstrate that electrospray ionization (ESI) mass spectrometry (MS) provides a convenient and effective way to probe both the structure of the conjugation products and their ability to interact with physiologically and therapeutically relevant partners, thereby providing important and valuable feedback that that can be used to refine and optimize the conjugation protocols and greatly facilitate the early stages of the drug development process.

Accordingly, aspects of the invention relate to novel biopharmaceuticals that can control CNS infections in an efficient way without eliciting a substantial immune response from the host. Further aspects relate to the use of transferrin (Tf) as a drug carrier that can deliver therapeutic proteins to cells and/or across physiological barriers (such as the blood-brain barrier). Chemical conjugation of a therapeutic payload (a small molecule medicine or a protein drug) to a transport protein, such as Tf, offers a convenient and inexpensive way to produce effective medicines that can be delivered to target tissues and cells. Thus, receptor-mediated transcytosis is utilized in some embodiments as a route to transport drugs across physiological barriers. TfR-specific antibodies may be used, for example, as a drug delivery vehicle, particularly for protein drugs targeting the CNS.

Furthermore, in this disclosure, Applicants demonstrate that ESI MS provide characterization of both the products and intermediates of protein-protein conjugation reactions at great detail. Native ESI MS analysis provides evidence that the conjugate is clearly recognized by the receptor. The ability of Lz-Tf to associate with TfR indicates that this species is capable of transferring from the bloodstream to the CNS via receptor-mediated transcytosis. ESI MS is used herein to evaluate retention of enzymatic activity of Lz following its conjugation to Tf. Since therapeutic targets of Lz (peptidoglycans from the cell walls of Gram-positive bacteria) may be too large and heterogeneous for direct ESI MS analysis, in some embodiments, studies use a trisaccharide molecule NAG3 as a surrogate substrate.

Compounds

In some embodiments, provided herein are compounds comprising transferrin receptor ligand covalently linked to a bactericidal agent. Accordingly, methods are provided herein for killing bacteria, e.g., gram-positive bacteria, and thus, for treating infections. In some embodiments, the methods involve contacting the bacteria with an inventive compound in an amount effective to breakdown the cell wall of the bacteria, thereby killing the bacteria. For example, the bacteria may be Staphylococci, *Listeria monocytogenes, Staphylococcus aureus, Stayphylococcus epidermidis, Steptococcus pneumonia, Diphtheroid bacilli, Propionobacterium acnes* or another infectious bacteria.

Transferrin Receptor Ligands

Transferrin receptor (TfR) is a carrier protein for transferrin. It is involved in the import of iron into cells and is regulated in response to intracellular iron concentration. It imports iron by internalizing the transferrin-iron complex through receptor-mediated endocytosis. Transferrin is present in blood plasma and brain extracellular fluids, and the transferrin receptor is present on brain capillary endothelial cells, choroid plexus epithelial cells, neurons, and probably also glial cells. The interaction between transferrin and transferrin receptor serve this function in the blood-brain, blood-CSF, and cellular-plasmalemma barriers.

As used herein, the term, "transferrin receptor ligand" is an agent that binds selectively to the transferrin receptor. The transferrin receptor ligand may be transferrin (e.g., human transferrin encoded by TF Gene ID: 7018). An exemplary transferrin sequence is provided as follows: >gi|4557871|ref|NP_001054.1| serotransferrin precursor [*Homo sapiens*]

[[MRLAVGALLVCAVLGLCLA]] {VPDKTVRWCAVSEHEATKCQSFRDHMKSVIP SDGPSVACVKKASYLDCIRAIAANEADAVTLDAGLVYDAYLAPNNLKPVVAEFYGSKE DPQTFYYAVAVVKKDSGFQMNQLRGKKSCHTGLGRSAGWNIPIGLLYCDLPEPRKPLE KAVANFFSGSCAPCADGTDFPQLCQLCPGCGCSTLNQYFGYSGAFKCLKDGAGDVAFV KHSTIFENLANKADRDQYELLCLDNTRKPVDEYKDCHLAQVPSHTVVARSMGGKEDLI WELLNQAQEHFGKDKSKEFQLFSSPHGKDLLFKDSAHGFLKVPPRMDAKMYLGYEYV TAIRNLREGTCPEAPTDECKPVKWCALSHHERLKCDEWSVNSVGKIECVSAETTEDCIA KIMNGEADAMSLDGGFVYIAGKCGLVPVLAENYNKSDNCEDTPEAGYFAVAVVKKSA SDLTWDNLKGKKSCHTAVGRTAGWNIPMGLLYNKINHCRFDEFFSEGCAPGSKKDSSL CKLCMGSGLNLCEPNNKEGYYGYTGAFRCLVEKGDVAFVKHQTVPQNTGGKNPDPW AKNLNEKDYELLCLDGTRKPVEEYANCHLARAPNHAVVTRKDKEACVHKILRQQQHL FGSNVTDCSGNFCLFRSETKDLLFRDDTVCLAKLHDRNTYEKYLGEEYVKAVGNLRKC STSSLLEACTFRRP} SEQ ID NO: 1. Note that the signal peptide is indicated by [[double brackets]] and assigned SEQ ID NO: 5, and the mature polypeptide is indicated by {braces} and assigned SEQ ID NO: 4.

Sequences of other examples of transferrin proteins that may be used as a transferrin receptor ligand in the compounds disclosed herein are found at GenBank Accession Numbers AAB22049.1 (*Homo sapiens*), AAP45055.1 (*Homo sapiens*), ABF47110.1 (*Homo sapiens*), XP_003925116 (*Saimiri boliviensis boliviensis*), NP_598738 (*Mus musculus*), AAH87021 (*Rattus norvegicus*), AAA30958 (*Equus caballus*) and NP_523401 (*Drosophila melanogaster*). The amino acid sequences of these transferrin proteins are incorporated herein by reference. In some embodiments, the transferrin receptor ligand is serotransferrin, lactotransferrin (lactoferrin), milk transferrin, egg white ovotransferrin (conalbumin), or membrane-associated melanotransferrin.

The transferrin receptor ligand may be a transferrin antibody or antigen-binding fragment that selectively binds to the transferrin receptor (e.g., Anti-Transferrin Receptor antibody [B349 (DF1513)] (ab8598) from Abcam®, Cambridge, Mass.; Transferring Receptor antibody NB100-92243 from Novus Biologicals, Littleton, Colo.); Sigma-Monoclonal Anti-CD71 (Transferrin Receptor) antibody from Sigma-Aldrich, St. Louis, Mo.).

The transferrin receptor ligand may be human hemochromatosis protein, *Machupo arenavirus* protein G, or other agent that binds selectively to the transferrin receptor.

Bactericidal Agent

As used herein, the term, "bactericidal agent" refers to a substance that kills bacteria. In some embodiments, a bactericidal agent kills Gram-positive bacteria. In some embodiments, a bactericidal agent kills Gram-negative bacteria. In some embodiments, a bactericidal agent kills Gram-negative bacteria and Gram-positive bacteria. In some embodiments, the bactericidal agent is a peptide. In some embodiments, a bactericidal agent is a host defense peptide (such as, for example, dermicidin, cathelicidins, defensins). In some embodiments the bactericidal agent is an endotoxin-neutralizing protein. In embodiments where the linker chemistry targets primary amino groups ($-NH_2$), bactericidal agents having $-NH_2$ groups may be used. However, in some embodiments, it is possible to modify molecules (e.g., transferrin receptor ligand, bactericidal agent) so that it suits the linker chemistry.

In some embodiments, the bactericidal agent is a glycoside hydrolase. Glycoside hydrolases (also called glycosidases or glycosyl hydrolases) catalyze the hydrolysis of the glycosidic linkage to release smaller sugars. Lysozymes, also known as muramidase or N-acetylmuramide glycanhydrolase, are glycoside hydrolases. In some embodiments, lysozymes are enzymes that damage bacterial cell walls by catalyzing hydrolysis of 1,4-beta-linkages between N-acetylmuramic acid and N-acetyl-D-glucosamine residues in a peptidoglycan and between N-acetyl-D-glucosamine residues in chitodextrins. Lysozyme may also be referred to as lysozyme C, renal amyloidosis, and 1,4-beta-N-acetylmuramidase C. In humans, the lysozyme enzyme is encoded by the LYZ gene.

An exemplary lysozyme enzyme has an amino acid sequence as follows: >gi|212276|gb|AAA48943.1| lysozyme ([*Gallus gallus*]

M[[RSLLILVLCFLPLAALG]]{KVFGRCELAAAMKRHGLDNYRGYSLGNWVCAA KFESNFNTQATNRNTDGSTDYGILQINSRWWCNDGRTPGSRNLCNIPCSALLSSDITASV NCAKKIVSDGNGMNAWVAWRNRCKGTDVQAWIRGCRL} SEQ ID NO: 2. Note that the signal peptide is indicated by [[double brackets]] and assigned SEQ ID NO: 6, and the mature polypeptide is indicated by {braces} and assigned SEQ ID NO: 3.

Sequences of other examples of lysozyme enzymes that may be used as in the compounds disclosed herein are found at GenBank Accession Numbers CAA32175.1 (*Homo sapiens*), AAP97222.1 (*Homo sapiens*), human—ACO37637.1 (*Homo sapiens*), CAA42797.1 (*Chlorocebus aethiops*), AAA39473.1 (*Mus musculus*), and AAA41552.1 (*Rattus norvegicus*). The amino acid sequences of these lysozyme enzymes are incorporated herein by reference.

While often the bactericidal agent is a glycoside hydrolase, in some embodiments, the bactericidal agent is a peptide selected from: Abacin, Andropin, Apidaecin IA, Apidaecin IB, Aurein 1.1, Aurein 1.2, Aurein 2.1, Aurein 2.2, Aurein 2.3, Aurein 2.4, Bactenecin, BACTENECIN 5, BACTENECIN 7, Bactericidin B-2, Ct-AMP1 and Dermaseptin-B2. Further peptides that may be used as bactericidal agents are disclosed in Jürgen Harder, et al., *Review: Human antimicrobial proteins—effectors of innate immunity*. Innate Immunity December 2007 vol. 13. no. 6 317-338, the contents of which relating to antimicrobial peptides are incorporated herein by reference.

Typically the bactericidal agent used herein is a peptide. However, in some embodiments, the bactericidal agent may be a small molecule (e.g., daptomycin, fluoroquinolones, metronidazole, nitrofurantoin, co-trimoxazole, telithromycin). In some embodiments, the bactericidal agent may be an aminoglycoside (e.g., amikacin, arbekacin, gentamicin, kanamycin, neomycin, netilmicin, paromomycin, rhodostreptomycin, streptomycin, tobramycin, and apramycin). In some embodiments, the bactericidal agent may be a Beta-lactam (e.g., penicillin derivatives (penams), cephalosporins (cephems), monobactams, and carbapenems) or vancomycin. In some embodiments, the bactericidal agent is a bacteriostatic agent, such as tetracycline, sulfonamide, spectinomycin, trimethoprim, chloramphenicol, macrolide, lincosamide or other agent.

In some embodiments, the bactericidal agent is not a ribosomal targeting agent. Ribosomal targeting agent target ribosomes at distinct locations within functionally relevant sites. They exert their inhibitory action by diverse modes, including competing with substrate binding, interfering with ribosomal dynamics, minimizing ribosomal mobility, facilitating miscoding, hampering the progression of the mRNA chain, and blocking the nascent protein exit tunnel. Examples of ribosomal targeting agent include the following: decoding (paromomycin); mRNA progression (spectinomycin); A-site binding to the small (tetracycline antibiotic) and the large (chloramphenicol) subunits; PTC mobility (sparsomycin); tRNA rotatory motion (quinupristin/dalfoprisin), and tunnel gating (troleandomycin); see Yonath, Annu. Rev. Biochem. (2005) 74:649-679. In certain embodiments, a ribosome targeting agent is a tetracycline antibiotic. Exemplary tetracycline antibiotics include, but are not limited to, tetracycline, chlortetracycline, oxytetracycline, demeclocycline, methacycline, sancycline, doxycline, aureomycin, terramycin, minocycline, 6-deoxytetracycline, lymecycline, meclocycline, methacycline, rolitetracycline, and glycylcycline antibiotics (e.g., tigecycline). However, in some embodiments, the bactericidal agent is a ribosomal targeting agent.

Features of Compounds

As disclosed herein, aspects of the invention relate to compounds comprising transferrin receptor ligand covalently linked to a bactericidal agent. In some embodiments, the compounds have the formula $X_1$-L-$X_2$, in which L is a linker that covalently links $X_1$ to $X_2$, $X_1$ is a transferrin receptor ligand, and $X_2$ is a bactericidal agent, e.g., a glycoside hydrolase. The compounds herein include a linker, L, that convalently links the transferrin receptor ligand to the bactericidal agent (e.g., glycoside hydrolase, e.g., lysozyme).

In some embodiments, the linker is a homobifunctional linker. However, in some embodiments, the linker is a heterobifunctional linker. In some embodiments, heterobifunctional linkers are advantageous because they help minimize the formation of homodimer conjugates.

In some embodiments, the linker is generating using a maleimide activated chemistry. In some embodiments, the linker is conjugated to the bactericidal agent and/or transferring receptor ligand utilizing SATA (N-succinimidyl S-acetylthioacetate) chemistry to modify the bactericidal agent and/or transferring receptor ligand. In some embodiments, the linker is conjugated to the bactericidal agent and/or transferring receptor ligand utilizing SATP (N-Succinimidyl S-Acetylthiopropionate) chemistry to modify the bactericidal agent and/or transferring receptor ligand. In some embodiments, the linker is conjugated to the bactericidal agent and/or transferring receptor ligand utilizing SAT(PEG)$_4$ (N-Succinimidyl S-acetyl(thiotetraethylene glycol)) chemistry to modify the bactericidal agent and/or transferring receptor ligand.

In some embodiments, the linker is a linear molecule of at least 30 Å, at least 50 Å in length, at least 100 Å in length, at least 200 Å or more in length. In some embodiments, the linker comprises a linear molecule having at least 10, at least 20, at least 30, at least 40, at least 50 rotatable bonds that are linearly arranged.

In some embodiments, the linker comprises polyethylene glycol (PEG)$_n$. In some embodiments n of (PEG)$_n$ is an integer up to 10, up to 20, up to 30, up to 40, up to 50, up to 60, up to 60, up to 70, up to 80, up to 90, up to 100 or more, the value of which is indicative of the number of units of (PEG) in the linker.

In some embodiments, compounds are provided of the formula

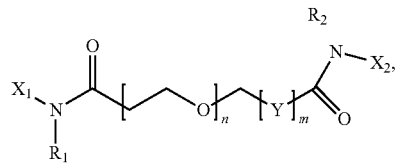

in which n is an integer from 1 to 100, and in which m is an integer from 1 to 4. In some embodiments, each instance of Y is independently selected from the group consisting of —N($R_3$)C(=O)—, —C(=O)N($R_3$)—, and —C($R_4$)$_2$—. In some embodiments, $R_1$, $R_2$, and each instance of $R_3$ are independently selected from the group consisting of hydrogen, optionally substituted C1-C6 alkyl, and a nitrogen protecting group; each instance of $R_4$ is independently selected from the group consisting of hydrogen, halogen, optionally unsubstituted acyl, optionally unsubstituted alkyl, optionally unsubstituted alkenyl, optionally unsubstituted alkynyl, optionally unsubstituted carbocyclyl, optionally unsubstituted heterocyclyl, optionally unsubstituted aryl, optionally unsubstituted heteroaryl, —OR$A$, —N(RA)2, —SRA, —CN, —SCN, —C(=NRA)RA, —C(=NRA) ORA, —C(=NRA)N(RA)$_2$, —C(=O)RA, —C(=O)ORA, —C(=O)N(RA)$_2$, —NO$_2$, —NRAC(=O)RA, —NRAC (=O)ORA, —NRAC(=O)N(RA)₂, —OC(=O)RA, —OC(=O)ORA, —OC(=O)N(RA)₂, and a nitrogen protecting group when attached to a nitrogen atom, or two $R_A$ groups are joined to form an optionally unsubstituted carbocyclic, optionally unsubstituted heterocyclic, optionally unsubstituted aryl, or optionally unsubstituted heteroaryl ring; and each instance of $R_A$ is independently selected from the group consisting of hydrogen, optionally unsubstituted acyl, optionally unsubstituted alkyl, optionally unsubstituted alkenyl, optionally unsubstituted alkynyl, optionally unsubstituted carbocyclyl, optionally unsubstituted heterocyclyl, optionally unsubstituted aryl, optionally unsubstituted heteroaryl, a nitrogen protecting group when attached to a nitrogen atom, an oxygen protecting group when attached to an oxygen atom, and a sulfur protecting group when attached to a sulfur atom, or two $R_A$ groups are joined to form an optionally unsubstituted heterocyclic ring.

In some embodiments, compounds are provided of the formula

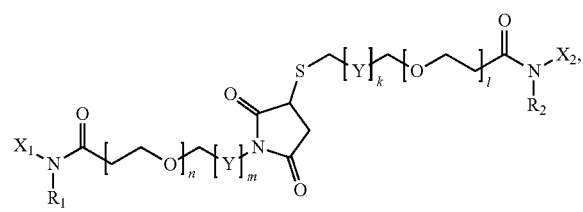

in which n and l are each independently an integer from 1 to 100 or an integer from 1 to 50, and in which m and k are each independently an integer from 1 to 4. In some embodiments, each instance of Y is independently selected from the group consisting of —N(R₃)C(=O)—, —C(=O)N(R₃)—, and —C(R₄)₂—. In some embodiments, $R_1$, $R_2$, and each instance of $R_3$ are independently selected from the group consisting of hydrogen, optionally substituted C1-6 alkyl, and a nitrogen protecting group; each instance of $R_4$ is independently selected from the group consisting of hydrogen, halogen, optionally unsubstituted acyl, optionally unsubstituted alkyl, optionally unsubstituted alkenyl, optionally unsubstituted alkynyl, optionally unsubstituted carbocyclyl, optionally unsubstituted heterocyclyl, optionally unsubstituted aryl, optionally unsubstituted heteroaryl, —ORA, —N(RA)2, —SRA, —CN, —SCN, —C(=NRA)RA, —C(=NRA)ORA, —C(=NRA)N(RA)₂, —C(=O)RA, —C(=O)ORA, —C(=O)N(RA)₂, —NO₂, —NRAC(=O)RA, —NRAC(=O)ORA, —NRAC(=O)N(RA)₂, —OC(=O)RA, —OC(=O)ORA, —OC(=O)N(RA)₂, and a nitrogen protecting group when attached to a nitrogen atom, or two $R_A$ groups are joined to form an optionally unsubstituted carbocyclic, optionally unsubstituted heterocyclic, optionally unsubstituted aryl, or optionally unsubstituted heteroaryl ring; and each instance of $R_A$ is independently selected from the group consisting of hydrogen, optionally unsubstituted acyl, optionally unsubstituted alkyl, optionally unsubstituted alkenyl, optionally unsubstituted alkynyl, optionally unsubstituted carbocyclyl, optionally unsubstituted heterocyclyl, optionally unsubstituted aryl, optionally unsubstituted heteroaryl, a nitrogen protecting group when attached to a nitrogen atom, an oxygen protecting group when attached to an oxygen atom, and a sulfur protecting group when attached to a sulfur atom, or two $R_A$ groups are joined to form an optionally unsubstituted heterocyclic ring.

In some embodiments, the compounds are of the formula

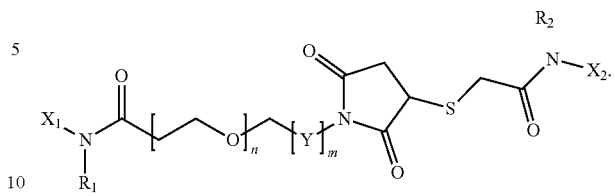

In some embodiments, the compounds are of the formula

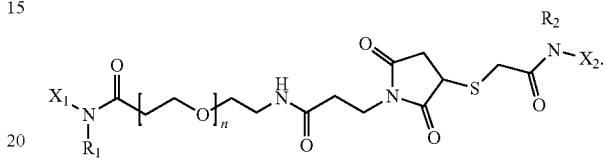

In some embodiments, the compounds are of the formula

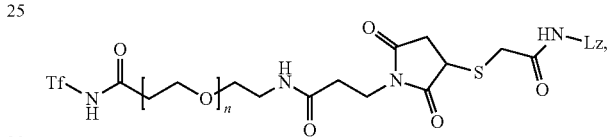

wherein Tf is transferrin and Lz is lysozyme. In some embodiments, n is in a range of 4-24 (e.g., 6, 8, 10, 11, 12, 13, 14)

The linker may be conjugated to amino groups in bactericidal agents. For example, when $X_1$ is transferrin the linker may be covalently linked to the transferrin at its N-terminal α-amino group or at an ε-amino group of any of its lysines. In some embodiments, the linker may be covalently linked to the transferrin at the ε-amino group of the lysine at amino acid position 4, 144, 196 or 280 (as set forth SEQ ID NO: 4 for the mature peptide) through an amide bond. Other potential lysine sites are at positions 41, 42, 102, 103, 115, 116, 304, 591, 593, 599, 640, 664 of transferrin (as set forth SEQ ID NO: 4 for the mature peptide).

Similarly, when $X_2$ is lysozyme the linker may be covalently linked to the lysozyme at its N-terminal α-amino group or at an ε-amino group of any of its lysines. In some embodiments, the linker may be covalently linked to the transferrin at the ε-amino group of the lysine at amino acid position 1, 13, 33, 96, 97, or 116, through an amide moiety (as set forth SEQ ID NO: 3 for the mature peptide).

In some embodiments, a multimeric compounds are provided. The multimeric compounds can form when a transferrin receptor ligand and a bactericidal agent form disulfide linkages between one another, for example. In some embodiments, the multimeric compounds form when linkers form covalent linkages between amino groups in transferrin receptor ligands and bactericidal agents. For example, multiple linkers may be conjugated to a particular bactericidal agent and/or transferrin receptor ligand and thus the bactericidal agent and/or transferrin receptor ligand may be covalently linked with multiple other ligands or agents. In some embodiments, the multimeric compounds comprise a plurality of covalently linked monomers having the formula [$X_1$-L-$X_2$], in which L is a linker that covalently links $X_1$ to $X_2$, in which $X_1$ is a transferrin receptor ligand, and $X_2$ is a glycoside hydrolase. For example, a multimeric complex may be of the formula: $X_1$-L-$X_2$-$X_2$-L-$X_2$ or $X_1$-L-$X_2$-$X_1$-L-$X_2$ where the $X_2$-$X_2$ or $X_2$-$X_1$ are joined together through disulfide linkages. More complex arrangements of the respective molecules can be formed, as depicted, for example, in FIG. 1C.

In some embodiments, compositions are provided that include pluralities of different compounds. For example, compounds may be provided that include a plurality of multimeric compounds of different forms. In some embodiments, chromatography is used to separate out compounds of a particular type or to obtain a particular purity level of a compound of a particular type.

In some embodiments, compositions are provided that comprise pluralities of compounds. In some embodiments, the compositions comprises at least 30%, at least 40%, at least 50%, at least 60%, at least 70%, at least 80%, at least 90%, at least 95%, at least 99% or more of a particular compound of interest. In some embodiments, composition are provided that comprise pluralities of different compounds, each of which compounds has a formula $X_1$-L-$X_2$ in which L is a linker that covalently links $X_1$ to $X_2$, and in which $X_1$ is a transferrin receptor ligand and $X_2$ is a bactericidal agent (e.g., glycoside hydrolase). In some embodiments, for at least 30%, at least 40%, at least 50%, at least 60%, at least 70%, at least 80%, at least 90%, at least 95%, at least 99% or more of the compounds in the plurality, the linker, L, is covalently linked to transferrin at its N-terminal α-amino group and/or to the bactericidal agent (e.g., glycoside hydrolase) at its N-terminal α-amino group.

In other embodiments, compositions are provided that comprise a mixture of compounds. In some embodiments, compositions are provided that comprise a mixture of compound in which at least 30%, at least 40%, at least 50%, at least 60%, at least 70%, at least 80%, at least 90%, at least 95%, at least 99% or more of the compounds in the mixture are monomeric compounds having the formula $X_1$-L-$X_2$, and in which the remaining compounds comprise (i) multimeric compounds comprising a plurality of covalently linked monomers having the formula [$X_1$-L-$X_2$], and/or (ii) complexes of two or more covalently linked glycoside hydrolases, in which L is a linker that covalently links $X_1$ to $X_2$, $X_1$ is a transferrin receptor ligand, and $X_2$ is a bactericidal agent (e.g., glycoside hydrolase).

Further Information Regarding Linkers

In some embodiments, the linkers are biocompatible. As used herein the term, "biocompatible" refers to a substances that does not cause severe toxicity, severe adverse biological reaction, or lethality in a subject (e.g., human) to which it is administered at reasonable doses and rates. In some embodiments, a biocompatible linker comprises a molecule having a Polar Surface Area (PSA) to Total Surface Area (TSA) ratio of at least 45%, at least 55%, at least 65%, at least 75%, or at least 85%.

In some embodiments, the linker is non-cleavable or resistant to cleavage inside the endosome of cells.

In some embodiments, the linker is a biodegradable linker that comprises one or more biodegradable segments. A "biodegradable linker" is one that, subsequent to administration within the subject or exposure to an enzyme, undergoes dissolution, degradation, resorption and/or other disintegration processes. In certain embodiments, the biodegradable linker degrades in vivo by both non-enzymatic and enzymatic hydrolysis. In certain embodiments, the biodegradable linker comprises one or more ester, thioester, or amide moieties, —C(=O)O—, —OC(=O)—, —C(=O)S—, —SC(=O)—, C(=O)NH—, —NHC (=O)—, which are cleavable in vivo by both non-enzymatic and enzymatic hydrolysis. In some embodiments, the cleavage products of the linker are non-toxic.

In certain embodiments, the linker comprises substituted or unsubstituted alkylene; substituted or unsubstituted alkenylene; substituted or unsubstituted alkynylene; substituted or unsubstituted heteroalkylene; substituted or unsubstituted heteroalkenylene; substituted or unsubstituted heteroalkynylene; substituted or unsubstituted heterocyclylene; substituted or unsubstituted carbocyclylene; substituted or unsubstituted arylene; substituted or unsubstituted heteroarylene; peptidyl groups; dipeptidyl groups; polypeptidyl groups; polymeric groups; and combinations thereof.

In certain embodiments, the linker comprises at least one instance of substituted or unsubstituted alkylene, e.g., substituted or unsubstituted C1-6 alkylene, substituted or unsubstituted C2-6 alkylene, substituted or unsubstituted C3-6 alkylene, substituted or unsubstituted C4-6 alkylene, substituted or unsubstituted C5-6 alkylene, substituted or unsubstituted C2-5 alkylene, substituted or unsubstituted C2-4 alkylene, substituted or unsubstituted C2-3 alkylene, substituted or unsubstituted C1 alkylene, substituted or unsubstituted C2 alkylene, substituted or unsubstituted C3 alkylene, substituted or unsubstituted C4 alkylene, substituted or unsubstituted C5 alkylene, or substituted or unsubstituted C6 alkylene.

In certain embodiments, the linker comprises at least one instance of substituted or unsubstituted alkenylene, e.g., substituted or unsubstituted C2-6 alkenylene, substituted or unsubstituted C3-6 alkenylene, substituted or unsubstituted C4-6 alkenylene, substituted or unsubstituted C5-6 alkenylene, substituted or unsubstituted C2-5 alkenylene, substituted or unsubstituted C2-4 alkenylene, substituted or unsubstituted C2-3 alkenylene, substituted or unsubstituted C2 alkenylene, substituted or unsubstituted C3 alkenylene, substituted or unsubstituted C4 alkenylene, substituted or unsubstituted C5 alkenylene, or substituted or unsubstituted C6 alkenylene.

In certain embodiments, the linker comprises at least one instance of substituted or unsubstituted alkynylene, e.g., substituted or unsubstituted C2-6 alkynylene, substituted or unsubstituted C3-6 alkynylene, substituted or unsubstituted C4-6 alkynylene, substituted or unsubstituted C5-6 alkynylene, substituted or unsubstituted C2-5 alkynylene, substituted or unsubstituted C2-4 alkynylene, substituted or unsubstituted C2-3 alkynylene, substituted or unsubstituted C2 alkynylene, substituted or unsubstituted C3 alkynylene, substituted or unsubstituted C4 alkynylene, substituted or unsubstituted C5 alkynylene, or substituted or unsubstituted C6 alkynylene.

In certain embodiments, the linker comprises at least one instance of substituted or unsubstituted heteroalkylene, e.g., substituted or unsubstituted hetero C1-6 alkylene, substituted or unsubstituted hetero C2-6 alkylene, substituted or unsubstituted hetero C3-6 alkylene, substituted or unsubstituted heteroC4-6 alkylene, substituted or unsubstituted hetero C5-6 alkylene, substituted or unsubstituted hetero C2-5 alkylene, substituted or unsubstituted hetero C2-4 alkylene, substituted or unsubstituted hetero C2-3 alkylene, substituted or unsubstituted hetero C1 alkylene, substituted or unsubstituted hetero C2 alkylene, substituted or unsubstituted hetero C3 alkylene, substituted or unsubstituted hetero C4 alkylene, substituted or unsubstituted hetero C5 alkylene, or substituted or unsubstituted hetero C6 alkylene.

In certain embodiments, the linker comprises at least one instance of substituted or unsubstituted heteroalkenylene, e.g., substituted or unsubstituted hetero C2-6 alkenylene, substituted or unsubstituted hetero C3-6 alkenylene, substituted or unsubstituted hetero C4-6 alkenylene, substituted or unsubstituted hetero C5-6 alkenylene, substituted or unsubstituted hetero C2-5 alkenylene, substituted or unsubstituted hetero C2-4 alkenylene, substituted or unsubstituted hetero C2-3 alkenylene, substituted or unsubstituted hetero C2 alkenylene, substituted or unsubstituted hetero C3 alkenylene, substituted or unsubstituted hetero C4 alkenylene, substituted or unsubstituted hetero C5 alkenylene, or substituted or unsubstituted hetero C6 alkenylene.

In certain embodiments, the linker comprises at least one instance of substituted or unsubstituted heteroalkynylene, e.g., substituted or unsubstituted hetero C2-6 alkynylene, substituted or unsubstituted hetero C3-6 alkynylene, substituted or unsubstituted hetero C4-6 alkynylene, substituted or unsubstituted hetero C5-6 alkynylene, substituted or unsubstituted hetero C2-5 alkynylene, substituted or unsubstituted hetero C2-4 alkynylene, substituted or unsubstituted hetero C2-3 alkynylene, substituted or unsubstituted hetero C2 alkynylene, substituted or unsubstituted hetero C3 alkynylene, substituted or unsubstituted hetero C4 alkynylene, substituted or unsubstituted hetero C5 alkynylene, or substituted or unsubstituted hetero C6 alkynylene.

In certain embodiments, the linker comprises at least one instance of substituted or unsubstituted heterocyclylene, e.g., substituted or unsubstituted 5- to 8-membered heterocyclylene, substituted or unsubstituted 5- to 7-membered heterocyclylene, substituted or unsubstituted 5- to 6-membered heterocyclylene, substituted or unsubstituted 5-membered heterocyclylene, substituted or unsubstituted 6-membered heterocyclylene, substituted or unsubstituted 7-membered heterocyclylene, or substituted or unsubstituted 8-membered heterocyclylene.

In certain embodiments, the linker comprises at least one instance of substituted or unsubstituted carbocyclylene, e.g., substituted or unsubstituted C3-6 carbocyclylene, substituted or unsubstituted C3-5 carbocyclylene, substituted or unsubstituted C3-4 carbocyclylene, substituted or unsubstituted C3 carbocyclylene, substituted or unsubstituted C4 carbocyclylene, substituted or unsubstituted C5 carbocyclylene, or substituted or unsubstituted C6 carbocyclylene.

In certain embodiments, the linker comprises at least one instance of substituted or unsubstituted arylene, e.g., substituted or unsubstituted C6 arylene (phenylene) or substituted or unsubstituted C10 arylene (naphthylene).

In certain embodiments, the linker comprises at least one instance of substituted or unsubstituted heteroarylene, e.g., substituted or unsubstituted 5-membered heteroarylene or substituted or unsubstituted 6-membered heteroarylene.

In certain embodiments, the linker comprises at least one instance of a peptidyl group as described herein. In certain embodiments, the linker comprises at least one instance of a dipeptidyl group as described herein.

Further examples of linkers for use in conjunction with the present invention, many of which are readily biodegradable, include, but are not limited to, cellulosic polymers and copolymers, for example, cellulose ethers such as methylcellulose (MC), hydroxyethylcellulose (HEC), hydroxypropyl cellulose (HPC), hydroxypropyl methyl cellulose (HPMC), methylhydroxyethylcellulose (MHEC), methylhydroxypropylcellulose (MHPC), carboxymethyl cellulose (CMC), hydroxyethylcarboxymethylcellulose (HECMC), carboxymethylhydroxyethylcellulose (CMHEC), other polysaccharides and polysaccharide derivatives such as starch (e.g., Hetastarch), dextran, dextran derivatives, chitosan, and alginic acid and its various salts, glycosaminoglycans and proteoglycans such as hyaluronic acid and its salts, other polymers, for example, polyhydroxyacids such as polylactide, polyglycolide, polyl(lactide-co-glycolide) and poly(epsilon.-caprolactone-co-glycolide)-, carboxyvinyl polymers and their salts (e.g., carbomer), polyvinylpyrrolidone (PVP), polyacrylic acid and its salts, polyacrylamide, polyacilic acid/acrylamide copolymer, polyalkylene oxides such as polyethylene oxide, polypropylene oxide, poly(ethylene oxide-propylene oxide), poloxomers, polyoxyethylene (polyethylene glycol, PEG), polyanhydrides, polyvinylalcohol, polyethyleneamine and polypyrridine, polymers of hydroxy acids such as lactic acid and glycolic acid polylactide, polyglycolide, polylactide co glycolide, and copolymers with PEG, polyanhydrides, poly(ortho)esters, polyurethanes, poly(butyric acid), poly(valeric acid), poly(lactide-co-caprolactone), salts, and copolymers thereof.

Treatment Methods and Related Compositions

Compounds provided herein are useful for targeting infections of the CNS because the transferrin receptor ligand facilitate passage across the blood-brain-barrier. Thus, the compounds can be delivering intravenously and still reach the CNS to treat an infection. In some embodiments, compounds provided herein are particularly useful for treating life-threatening infections of the CNS, such as bacterial meningitis. Accordingly, in some embodiments, methods are provided herein for treating a bacterial infection of the central nervous system (CNS) in a subject. In some embodiments, methods provided herein involve administering to the CNS of the subject a pharmaceutical composition comprising an inventive compound in an amount effective for treating a bacterial infection in the CNS. For example, the administration may involve delivering the composition to the subject intravenously, in which the compound enters the CNS by crossing the blood-brain-barrier through interactions between the transferrin receptor ligand and the transferrin receptor.

The term "subject," as used herein, generally refers to a mammal. Typically the subject is a human. However, the term embraces other species, e.g., pigs, mice, rats, dogs, cats, or other primates. In certain embodiments, the subject is an experimental subject such as a mouse or rat. The subject may be a male or female. The subject may be an infant, a toddler, a child, a young adult, an adult or a geriatric. In some embodiments, the subject has or is suspected of having bacterial meningitis or other bacterial infection.

In some embodiments, treatment is performed after diagnosing a subject as having a bacterial infection. In some embodiments, prior to treating a subject with a compound disclosed herein a healthcare provider may first determine that the subject has a bacterial infection using an appropriate test. For example, the healthcare provider may determine that the subject has a bacterial infection and further determine whether the infection is of a Gram-negative or Gram positive bacteria. Armed with this information the healthcare provider may then select an appropriate compound for treating the subject. For example, if the subject is identified as having a bacterial infection of a Gram-positive bacteria, then the healthcare provider may select a compound comprising a glycoside hydrolase, such as, a lysozyme, that kills Gram-positive bacteria. Any appropriate test may be used to detect presence of Gram-positive or -negative bacteria in the CNS fluid, including, for example, a Gram stain assay or PCR assay.

For purposes of treating bacterial infections, compounds may be administered in sufficient amounts to reach cells of a desired tissue, e.g., CNS tissue, and to provide sufficient levels of compounds in cells of that tissue without undue adverse effects. It is generally desirable to administer the compounds in a sufficient dose and via an appropriate route to ensure that they reach brain tissue, meninges, neuronal cells, glial cells, astrocytes, oligodendrocytes, cerebrospinal fluid (CSF), interstitial spaces or other aspect of the CNS. Typically, the compounds are administered intravascularly, e.g., intravenously, as they are generally capable of crossing the blood brain barrier. Administration into the bloodstream may be by injection into a vein, an artery, or any other vascular conduit. However, any conventional and pharmaceutically acceptable routes of administration may be used. These include, but are not limited to, direct delivery to the selected tissue (e.g., intracerebral administration, intrathecal administration), intravenous, oral, inhalation (including intranasal and intratracheal delivery), intraocular, intramuscular, subcutaneous, intradermal, intratumoral, and other parental routes of administration. Routes of administration may be combined, if desired.

The compounds of the invention also may be administered at a dose effective in treating infection in a subject as determined using standard techniques. "Treating infection" refers to a significant decrease in the signs and symptoms of infection. For example, but not by way of limitation, symptomatic relief, in which a patient is rendered subjectively relieved of discomfort or the risk of a progressive infection or sepsis, would be considered as satisfactory results of therapy. In some embodiments of the invention, the compounds may be administered to a subject (e.g., a human patient) at a dose of about 2.5 mg/kg to about 500 mg/kg. In some embodiments, the dose is up to about 1 mg/kg, up to about 10 mg/kg, up to about 50 mg/kg, up to about 100 mg/kg, up to about 200 mg/kg, up to about 500 mg/kg or more. The dose may be administered at appropriate intervals, e.g., but not limited to, daily, or once, twice, or three times a week.

The compounds may be formulated as compounds with a suitable carrier. Suitable carriers may be readily selected by one of skill in the art. For example, one suitable carrier includes saline, which may be formulated with a variety of buffering solutions (e.g., phosphate buffered saline). Other exemplary carriers include sterile saline, lactose, sucrose, calcium phosphate, gelatin, dextran, agar, pectin, peanut oil, sesame oil, and water. The selection of the carrier is not a limitation of the present invention. Optionally, the compositions of the invention may contain, in addition to the compounds and carrier(s), other conventional pharmaceutical ingredients, such as preservatives, or chemical stabilizers. Suitable exemplary preservatives include chlorobutanol, potassium sorbate, sorbic acid, sulfur dioxide, propyl gallate, the parabens, ethyl vanillin, glycerin, phenol, and parachlorophenol. Suitable chemical stabilizers include gelatin and albumin.

Formulation of pharmaceutically-acceptable excipients and carrier solutions is well-known to those of skill in the art, as is the development of suitable dosing and treatment regimens for using the particular compositions described herein in a variety of treatment regimens. Typically, these formulations may contain at least about 0.1% of the active ingredient or more, although the percentage of the active ingredient(s) may, of course, be varied and may conveniently be between about 1 or 2% and about 70% or 80% or more of the weight or volume of the total formulation. Naturally, the amount of active ingredient in each therapeutically-useful composition may be prepared is such a way that a suitable dosage will be obtained in any given unit dose of the compound. Factors such as solubility, bioavailability, biological half-life, route of administration, product shelf life, as well as other pharmacological considerations will be contemplated by one skilled in the art of preparing such pharmaceutical formulations, and as such, a variety of dosages and treatment regimens may be desirable.

The pharmaceutical forms suitable for injectable use include sterile aqueous solutions or dispersions and sterile powders for the extemporaneous preparation of sterile injectable solutions or dispersions. Dispersions may also be prepared in glycerol, liquid polyethylene glycols, and mixtures thereof and in oils. Under ordinary conditions of storage and use, these preparations contain a preservative to prevent the growth of microorganisms. In many cases the form is sterile and fluid to the extent that easy syringability exists. It must be stable under the conditions of manufacture and storage and must be preserved against the contaminating action of microorganisms, such as bacteria and fungi. The carrier can be a solvent or dispersion medium containing, for example, water, ethanol, polyol (e.g., glycerol, propylene glycol, and liquid polyethylene glycol, and the like), suitable mixtures thereof, and/or vegetable oils. Proper fluidity may be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars or sodium chloride. Prolonged absorption of the injectable compositions can be brought about by the use in the compositions of agents delaying absorption, for example, aluminum monostearate and gelatin.

For administration of an injectable aqueous solution, for example, the solution may be suitably buffered, if necessary, and the liquid diluent first rendered isotonic with sufficient saline or glucose. These particular aqueous solutions are especially suitable for intravenous, intramuscular, subcutaneous and intraperitoneal administration. In this connection, a sterile aqueous medium that can be employed will be known to those of skill in the art. For example, one dosage may be dissolved in 1 ml of isotonic NaCl solution and either added to 1000 ml of hypodermoclysis fluid or injected at the proposed site of infusion, (see for example, "Remington's Pharmaceutical Sciences" 15th Edition, pages 1035-1038 and 1570-1580). Some variation in dosage will necessarily occur depending on the condition of the host. The person responsible for administration will, in any event, determine the appropriate dose for the individual host.

Sterile injectable solutions are prepared by incorporating the active compound in the required amount in the appropriate solvent with various of the other ingredients enumerated herein, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

The compositions disclosed herein may also be formulated in a neutral or salt form. Pharmaceutically-acceptable salts, include the acid addition salts (formed with the free amino groups of the protein) and which are formed with inorganic acids such as, for example, hydrochloric or phosphoric acids, or such organic acids as acetic, oxalic, tartaric, mandelic, and the like. Salts formed with the free carboxyl groups can also be derived from inorganic bases such as, for example, sodium, potassium, ammonium, calcium, or ferric hydroxides, and such organic bases as isopropylamine, trimethylamine, histidine, procaine and the like. Upon formulation, solutions will be administered in a manner compatible with the dosage formulation and in such amount as is therapeutically effective. The formulations are easily administered in a variety of dosage forms such as injectable solutions, drug-release capsules, and the like.

The phrase "pharmaceutically-acceptable" refers to molecular entities and compositions that do not produce an allergic or similar untoward reaction when administered to a host.

Kits and Related Compositions

The compounds described herein may, in some embodiments, be assembled into pharmaceutical or research kits to facilitate their use in therapeutic or research applications. A kit may include one or more containers housing the components of the invention and instructions for use. Specifically, such kits may include one or more compounds described herein, along with instructions describing the intended application and the proper use of these compounds. In certain embodiments agents in a kit may be in a pharmaceutical formulation and dosage suitable for a particular application and for a method of administration of the agents. Kits for research purposes may contain the components in appropriate concentrations or quantities for running various experiments.

The kit may be designed to facilitate use of the methods described herein by researchers and can take many forms. Each of the compositions of the kit, where applicable, may be provided in liquid form (e.g., in solution), or in solid form, (e.g., a dry powder). In certain cases, some of the compositions may be constitutable or otherwise processable (e.g., to an active form), for example, by the addition of a suitable solvent or other species (for example, water), which may or may not be provided with the kit.

As used herein, "instructions" can define a component of instruction and/or promotion, and typically involve written instructions on or associated with packaging of the invention. Instructions also can include any oral or electronic instructions provided in any manner such that a user will clearly recognize that the instructions are to be associated with the kit, for example, audiovisual (e.g., videotape, DVD, etc.), Internet, and/or web-based communications, etc. The written instructions may be in a form prescribed by a governmental agency regulating the manufacture, use or sale of pharmaceuticals or biological products, which instructions can also reflects approval by the agency of manufacture, use or sale for animal administration.

The kit may contain any one or more of the components described herein in one or more containers. As an example, in one embodiment, the kit may include instructions for mixing one or more components of the kit and/or isolating and mixing a sample and applying to a subject. The kit may include a container housing agents described herein. The agents may be in the form of a liquid, gel or solid (e.g., powder). The agents may be prepared sterilely, packaged in syringe and shipped refrigerated. Alternatively it may be housed in a vial or other container for storage. A second container may have other agents prepared sterilely. Alternatively the kit may include the active agents premixed and shipped in a syringe, vial, tube, or other container. The kit may have one or more or all of the components required to administer the agents to a subject, such as a syringe, topical application devices, or IV needle tubing and bag.

Exemplary embodiments of the invention will be described in more detail by the following examples. These embodiments are exemplary of the invention, which one skilled in the art will recognize is not limited to the exemplary embodiments.

EXAMPLES

Example 1: Materials and Methods

Preparation of Lz-Tf Conjugate.

Figure 1B:
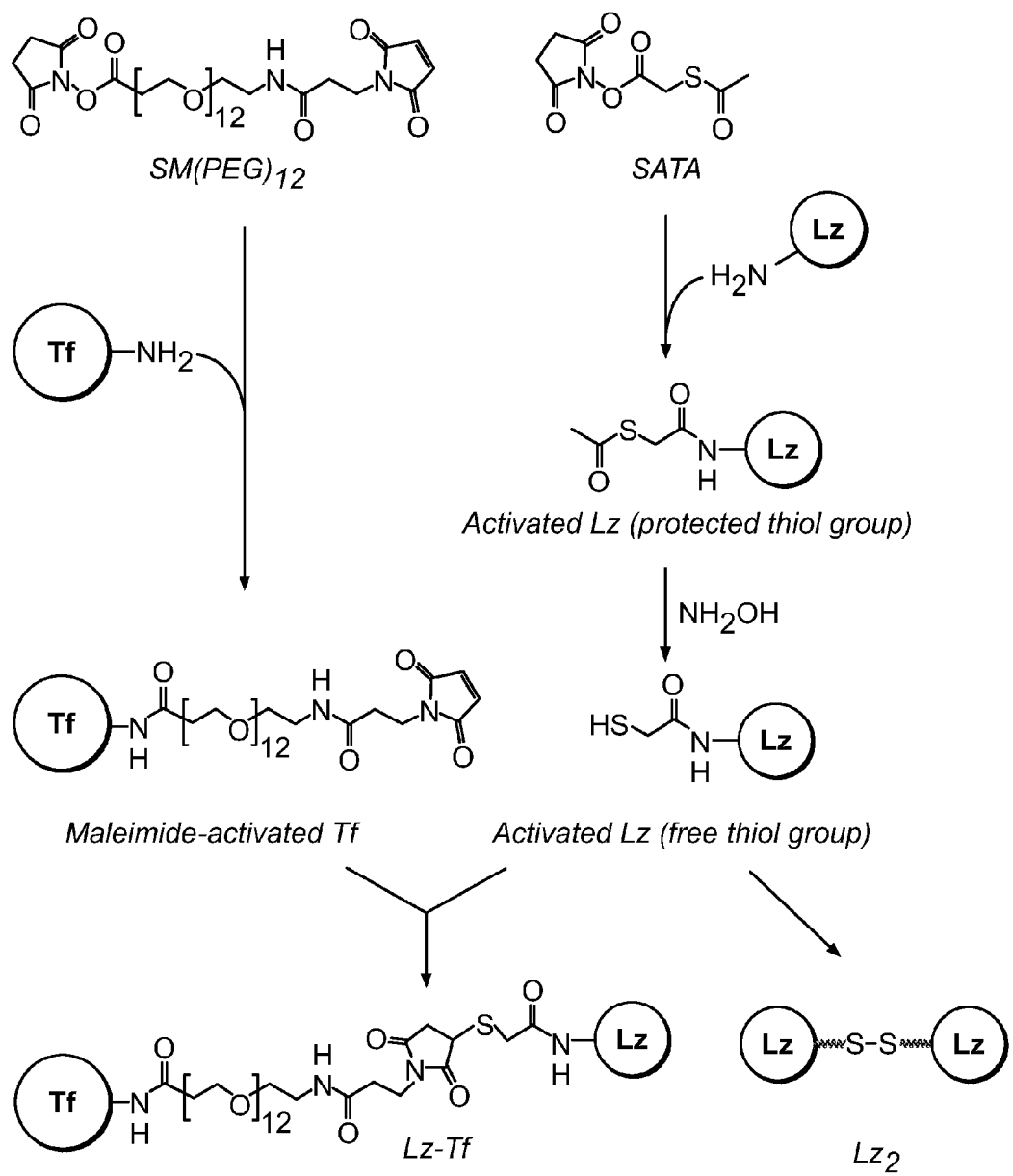

For each reaction the optimal final conditions are given in the text while various reaction parameters tested during optimization are listed in parenthesis. Lz from chicken egg white (Sigma-Aldrich, St. Louis, Mo.) was activated (decorated with free thiol groups) using either Traut's reagent (2-iminothiolane hydrochloride; Sigma-Aldrich, St. Louis, Mo.) or N-succinimidyl-S-acetylthioacetate (SATA; Pierce Biotechnology, Rockford, Ill.), which target primary amine groups. The reaction was carried out by incubating 12 h (0.5, 0.75, 1, 2, 12, 24 h) at 0° C. (0, 4, 25, 37° C.) in 50 mM phosphate buffer with 100 mM NaCl pH 8.0 (7.0, 7.5, 8.0, 8.5, 9.0) and consisted of 500 µM (50, 100, 250, 500 µM) Lz with a 1:1 ratio (2:1, 1:1, 1:2, 1:4) of primary amines relative to the thiolating reagent (freshly prepared in $H_2O$). Incorporation of thiol-reactive maleimide groups into human Tf was carried out by reacting with either sulfosuccinimidyl-4-[N-maleimidomethyl] cyclohexane-1-carboxylate (sulfo-SMCC: Pierce Biotechnology, Rockford, Ill.) or succinimidyl-([N-maleimidopropionamido]-dodecaethyleneglycol) ester $(SM(PEG)_{12}$; Pierce Biotechnology, Rockford, Ill.) for 90 min (30, 60, 90, 120 min) at 25° C. (4, 25, 37° C.) in 50 mM phosphate buffer with 100 mM NaCl pH 7.0 (6.0, 7.0, 8.0, 9.0) and consisted of 250 µM (50, 100, 250 µM) Tf with a 1:2 (1:2, 1:4, 1:20) ratio of Tf relative to the activating reagent (freshly prepared in DMSO). Excess activation reagents were removed by centrifugal filtration through a 10 kDa Vivaspin molecular weight filter (Sartorius Stedim Biotech SA, Bohemia, N.Y.) and the non-cleavable thioether linkage between activated Lz and Tf was formed by incubating 50 µM (25, 50, 100 µM) each of the two modified proteins together for 12 h (1, 2, 4 h, 12, 24 h) at 4° C. (4, 25, 37° C.) in 50 mM phosphate buffer with 100 mM NaCl, pH 7.0 (7.0, 8.0, 9.0) at 1:1 molar ratio. The 1:1 Lz-Tf conjugate was isolated by cation exchange chromatography on a 4.6×100 mm PolyCATA™ column (5 µM, 1000 Å, PolyLC Inc., Columbia, Md.) using an Agilent 1100 (Agilent Technologies, Palo Alto, Calif.) HPLC system. All relevant reaction diagrams are shown in FIG. 1.

Mass Spectrometry.

ESI MS measurements were carried out with a QStar-XL (ABI/SCIEX, Toronto, Canada) hybrid quadrupole/time-of-flight MS equipped with a nanospray source. Mass profiling of activated Tf, activated Lz, the crude reaction product mixture, and the 1:1 conjugate isolated by cation exchange LC was carried out following buffer-exchange of proteins and placing them in water/methanol/acetic acid (49:49:2) at a concentration of ca. 10 µM. Native ESI MS analyses of the conjugate, and its mixtures with TfR and $NAG_3$ were performed using 20 mM ammonium acetate as a solvent. To maintain integrity of non-covalent complexes in the gas phase, the declustering potential in the ESI MS interface (DP1) was minimized, unless noted otherwise. Ectodomain of transferrin receptor (TfR) was used in binding assays, and N-acetylglucosamine trimer (NAG$_3$) was purchased from Sigma-Aldrich (St. Louis, Mo.).

Antimicrobial Activity Assay.

Antimicrobial activity of intact Lz, Lz dimers and Lz-Tf conjugate was measured using re-suspended dried cells of *Micrococcus lysodeikticus* (Worthington Biochemical Corp., Lakewood, N.J.) as the substrate. The rate of cell wall lysis in 0.1 M sodium phosphate buffer pH 7.0 at 25° C. was monitored by recording the transmission at 450 nm. The measurements were carried out in a 1 mL cuvette with a NanoDrop 2000c (Thermo Fisher Scientific, Rockford, Ill.) UV-Vis spectrophotometer.

TABLE 1

Bacteriolytic activity of Lz-Tf and related proteins

| Samples | Rate (mAU/min) | Specific activity (%) |
|---|---|---|
| Blank (negative control) | 0.0 | 0.0 |
| Tf (20 µM) | 0.0 | 0.0 |
| Lz control (2.5 µM) | 124 | 100 |
| Lz-Tf conjugate (6.7 µM) | 1.5 | 0.45 |
| Lz-Tf conjugate (30.6 µM) | 6.4 | 0.42 |
| Lz-Tf longer linker (6 µM) | 35 | 11.8 |
| Lz dimer 2IT(7.5 µM) | 138 | 18.6 |
| Lz dimer SATA (2.5 µM) | 125 | 50.6 |

Ion Exchange Chromatography Protocol
(Used for Isolating/Purifying the 1:1 Conjugate)
Solvents: A: 50 mM Sodium phosphate buffer, pH 6.5-7.0
  B: 50 mM Sodium phosphate buffer, 400 mM NaCl, pH 6.5-7.0
Flowrate: 1 mL/min
Gradient:

| Time (min) | %B |
|---|---|
| 0 | 0 |
| 5 | 0 |
| 20 | 50 |
| 21 | 100 |
| 26 | 100 |
| 27 | 0 |
| 30 | 0 |

Figure 3C:
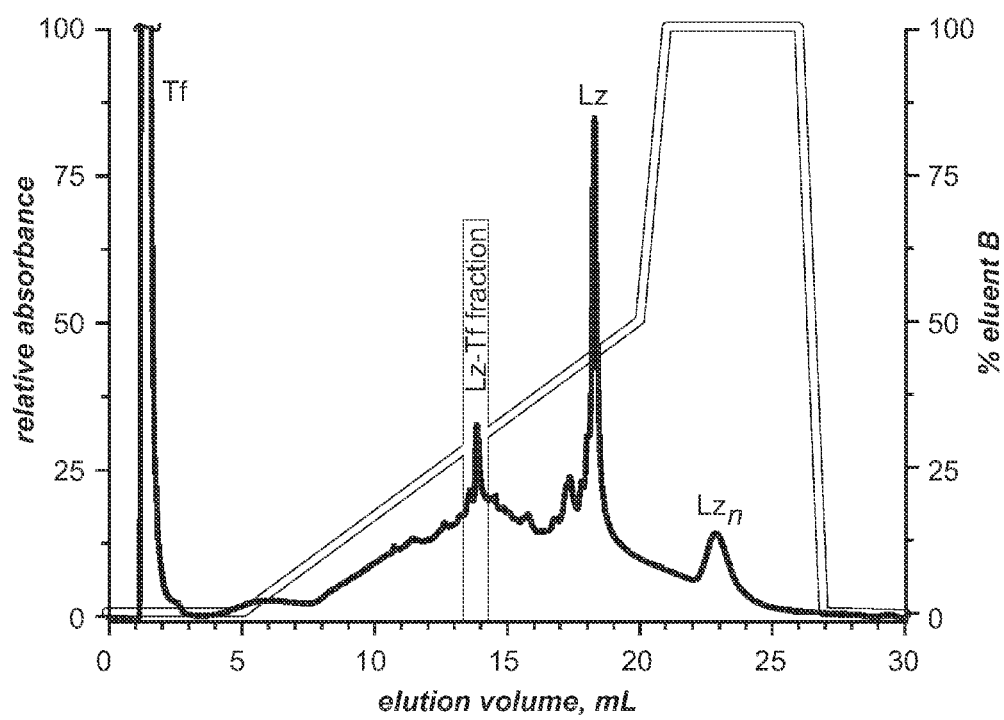

Significant difference between the pI values of Tf (5.5-6.3) and Lz (11.0) made ion exchange chromatography (IXC) useful as a means of separating the reaction products from each other and from reagents and reaction by-products. Using phosphate buffer, pH 6.5, and a shallow gradient Applicants have been achieved separation between the Tf and Lz peaks exceeding 15 minutes (FIG. 3C), with Lz homo-polymers having even longer elution times. The products of the Lz/Tf conjugation reaction elute within a wide (9-17 min) time period and are mostly unresolved, although a distinct peak is observed at 14 min elution time. IEC_Lz-SATA-SM(PEG)12-Tf (chromatogram for the conjugate with a shorter linker is shown in FIG. 3C of the manuscript Selection of Conjugates with "Desirable" Location(s) of the Linker Attachment Sites.

Figure 9A:
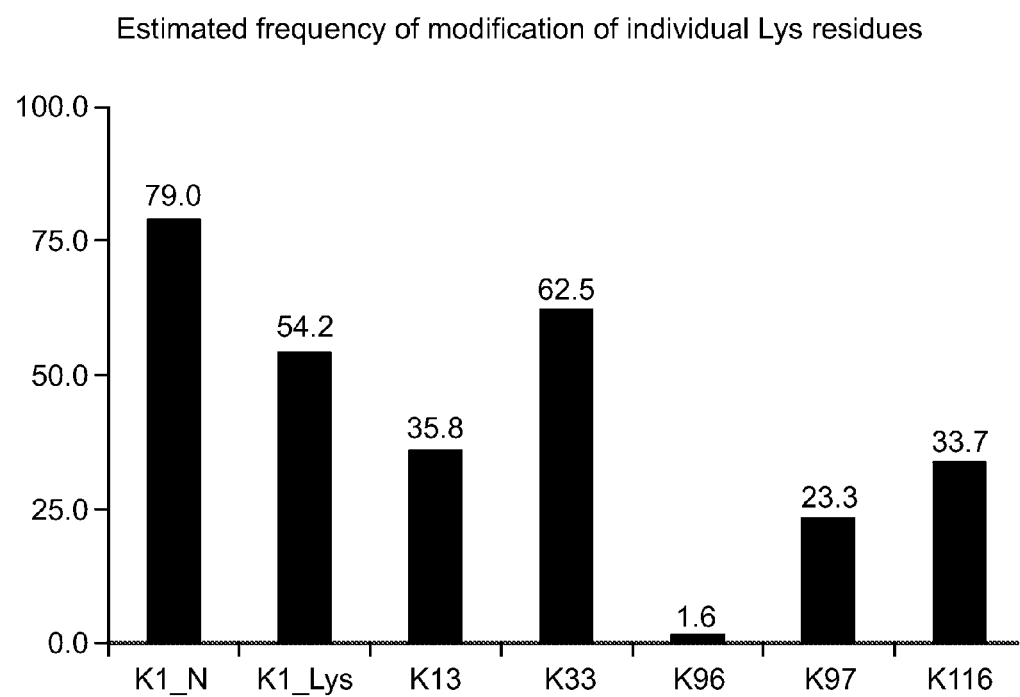
FIG. 9A. Estimated frequency of modification of individual Lys residues (based on LC/MS/MS analysis of the modified and intact proteins).
Figure 9B:
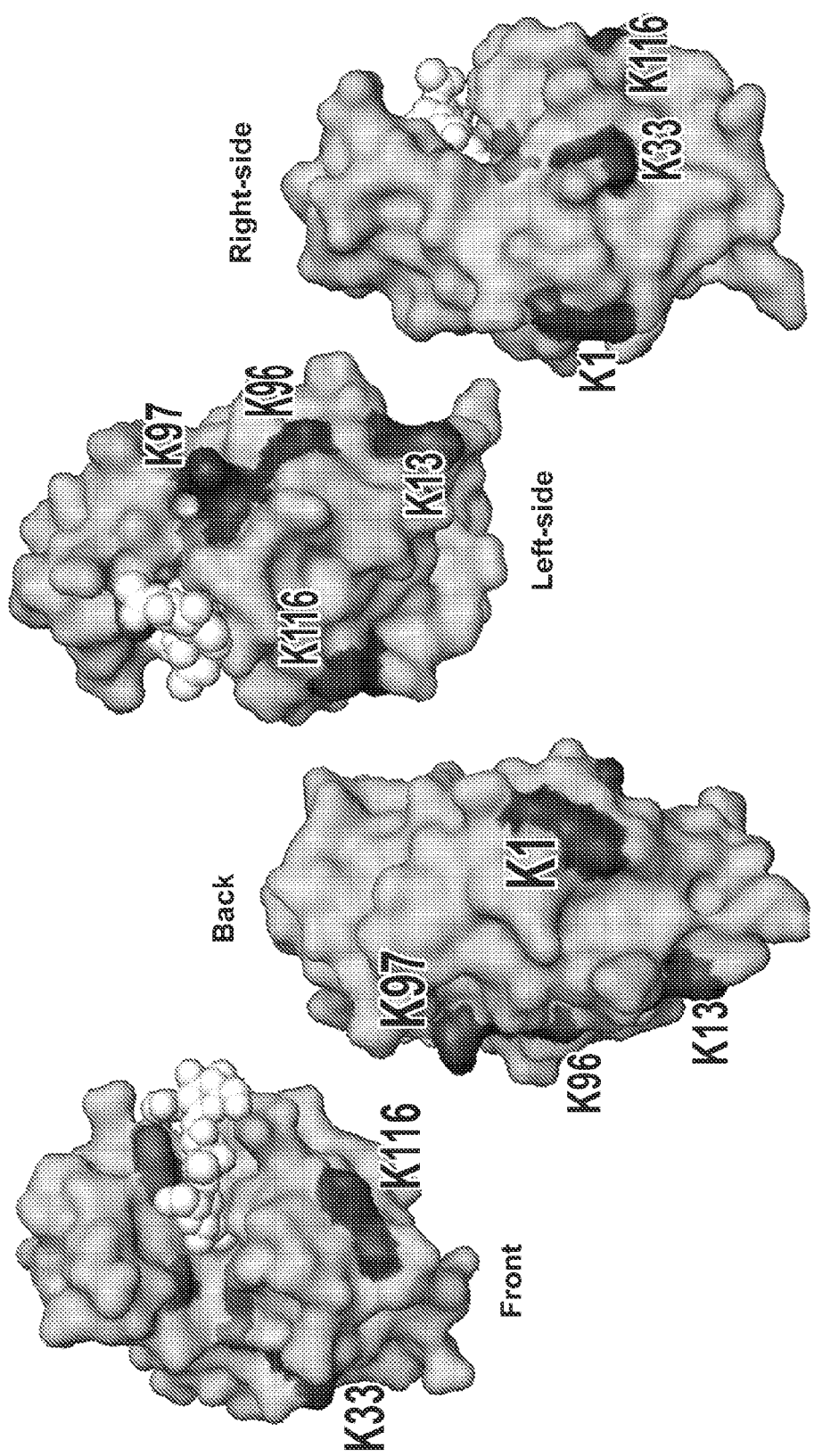
FIG. 9B. Surface charge model showing linker attachment site in Lz.

Data indicate that alpha-amine at the protein's N-terminal is a desirable modification site for both Lz and Tf in some cases. In some embodiments, selectivity is due to the lower pKa of α-amines compared to those of ε-amines (Lys side chains). Modification at the Lz N-terminal (either α-amine or ε-amine of Lys-1) is desirable, in some embodiments, since this site is the remote from the catalytic cavity of the enzyme and may minimally inter with the biological (bacteriolytic) activity of Lz. Likewise, the N-terminal of Tf is remote from the receptor-binding interface and is expected to cause least interference with the Tf/TfR interaction critical for the successful passage of the blood-brain barrier. (See FIGS. 8 and 9) In some embodiments, modification sites of Tf (based on LC/MS/MS) are at N terminal and amino acids K4, K144, K196, K280. In some embodiments, modification sites of Lz (based on LC/MS) are at N terminal and amino acids K1, K13, K33, K96, K97, and K116.

While modulating the pH provides some selectivity in targeting the α-amines of both proteins (lower pH value may favor α-amines over ε-amines), the product mixture may display heterogeneity. Further selection of "desirable" conjugates may be performed using affinity chromatography. Affinity of the lysozyme moiety of the Lz-Tf towards short N-acetylglucosamine (NAG) oligomers may be used to purify the complex. Selected NAG oligomers with a high affinity towards Lz may be immobilized to a support matrix (e.g. epoxide activated polystyrene resin) and a protein mixture containing Lz-Tf passed over the resin under physiological conditions (pH and ionic strength) allowing Lz-Tf to bind the resin. Elution of Lz-Tf may be achieved by increasing the ionic strength of the mobile phase. Utilizing a salt gradient for elution will allow fractionation of a heterogeneous mixture of bound Lz-Tf based on binding affinity towards the substrate analog.

Example 2: Production, Purification and Characterization of the Lz-Tf Conjugate

The scheme of conjugating Tf to a protein payload involves derivatization of Lys side chains on Tf with sulfo-SMCC and on the protein payload with the Traut's reagent, followed by reacting them with each other. This produces the same thio-ether linkage that was used in production of TransMID, the only Tf-based biopharmaceutical product that ever reached Phase III clinical trials. Placing a single maleimide group on Tf and a single free thiol group on Lz led to the formation of a 1:1 conjugate, with Lz dimer being the only by-product that can form via external disulfide bond formation (FIG. 1). The extent of Tf functionalization with sulfo-SMCC and Lz with Traut's reagent can be varied over a wide range. The extent of activation of the two proteins was not limited to a single reactive group on each polypeptide chain (FIG. 2), and adequate yields of the conjugation reaction can be achieved when multiple activation groups are placed on each protein.

Figure 1C:
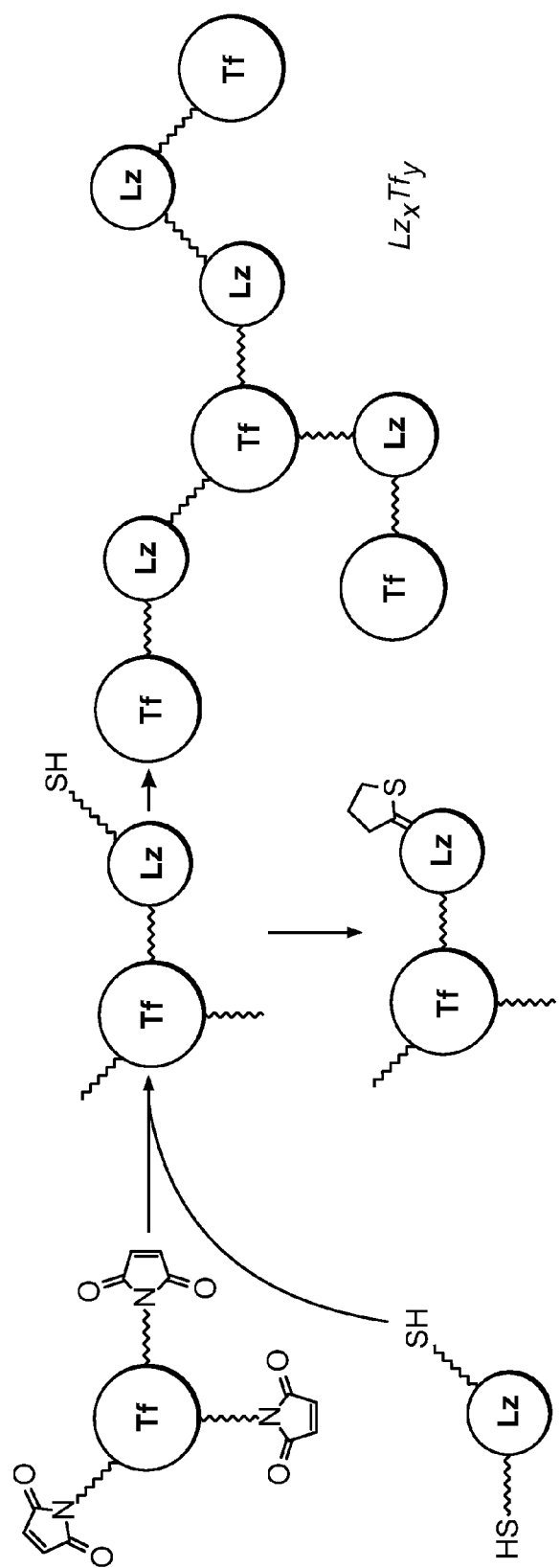

Placing multiple free thiol groups on Lz may increase the incidence and extent of this protein's polymerization via formation of external disulfide linkages. This process was found to occur with homo-polymerization of functionalized Tf (at neutral pH maleimide groups are ca. 1000 less reactive towards free amines compared to free sulfhydryls). Homo-polymerization was apparent when concentrations of Tf in the reaction mixture were elevated compared to that of the activated payload (Lz). This may beto the presence of a large number of free amine groups (Lys side chains) on the surface of Tf. Polyvalent functionalization of Tf and Lz was expected to contribute to the extent of heterogeneity of the conjugation products (FIG. 1C). Balancing the extent of modification of each protein in order to optimize production of the 1:1 Lz-Tf conjugate was achieved in this work by controlling reagent concentrations, temperature, incubation time and reaction pH. Mass spectrometry enabled us to determine the effect of altering these variables on the product, allowing us to screen these parameters in an iterative fashion that sought to improve the yield of conjugation while minimizing undesirable side reactions.

Figure 2A:
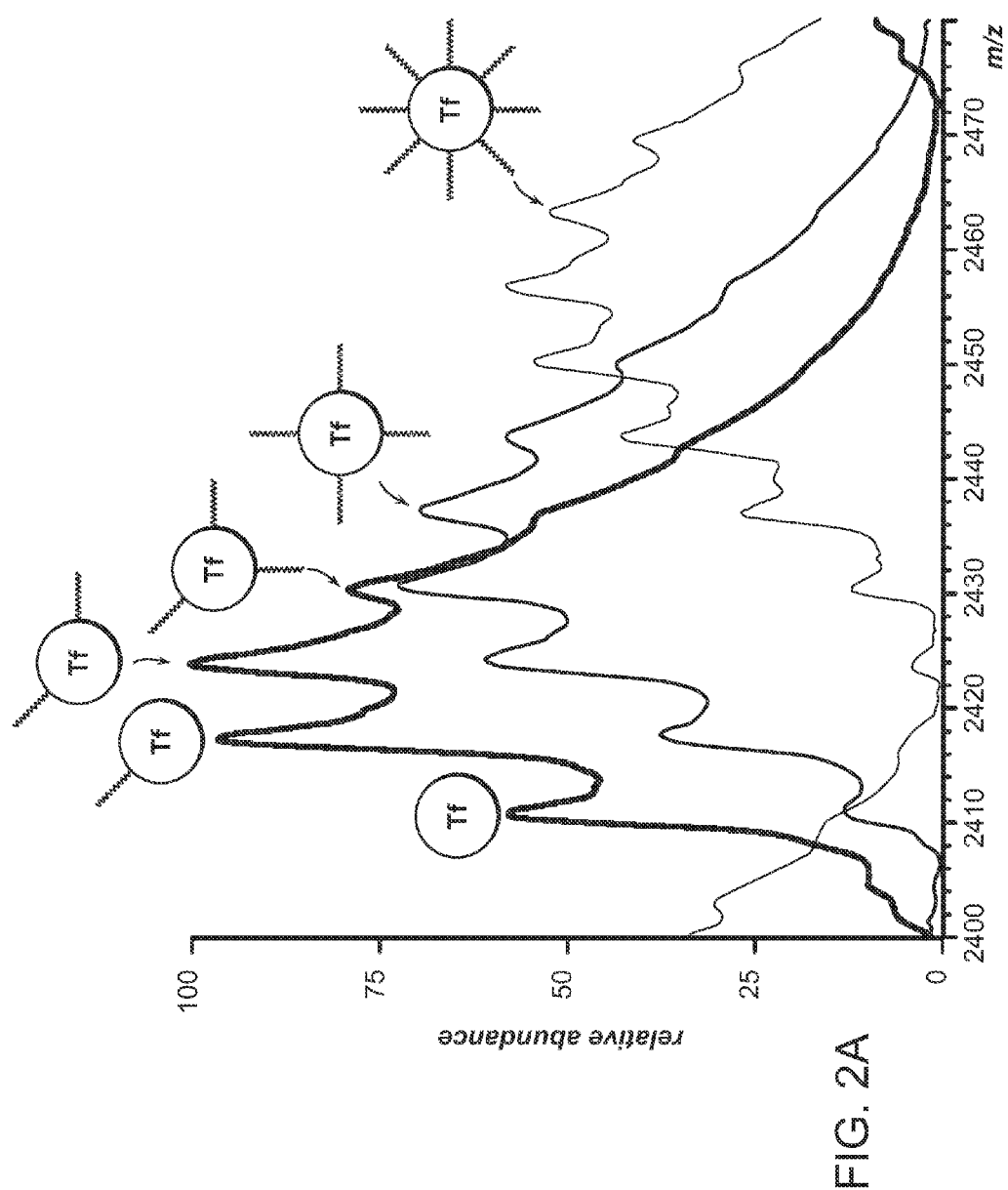
FIGS. 2A-2D. ESI mass spectra of activated Tf, charge state +32 (FIG. 2A) and Lz, charge state +10 (FIG. 2B) showing a range of reactive groups attached to the surface of each protein. The three traces shown in FIG. 2A correspond to a 1:2, 1:4 and 1:20 concentration ratio of Tf to sulfo-SMCC in the reaction. The multiple peaks shown in FIG. 2B are due to the presence of both chemically active (thiols) and de-activated (rings) groups on the surface of Lz. All mass spectra were acquired under denaturing condition (10 μM total protein concentration in water/methanol/acetic acid, 49:49:2 by volume).
Figure 2B:
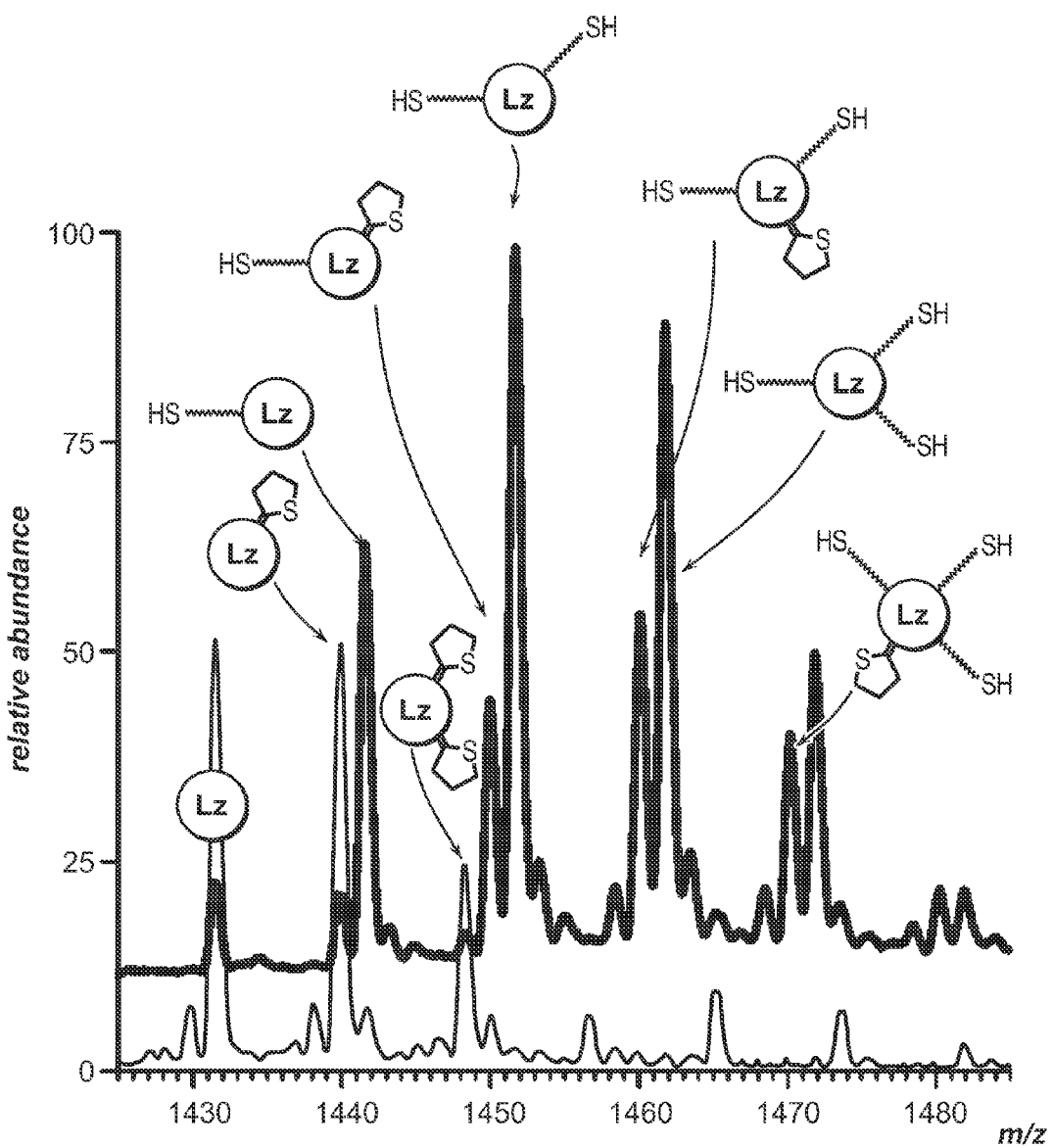
Figure 2C:
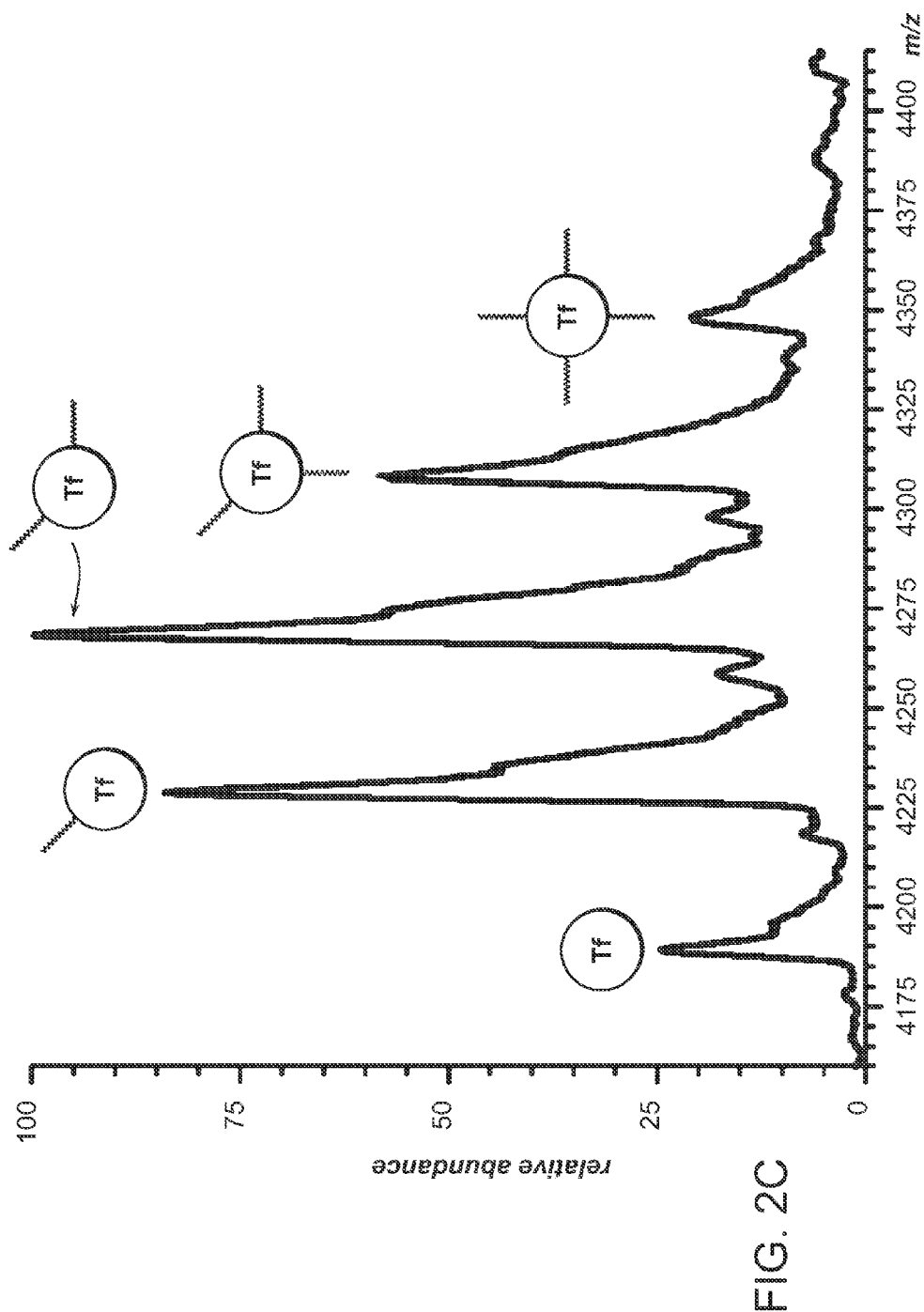
Figure 2D:
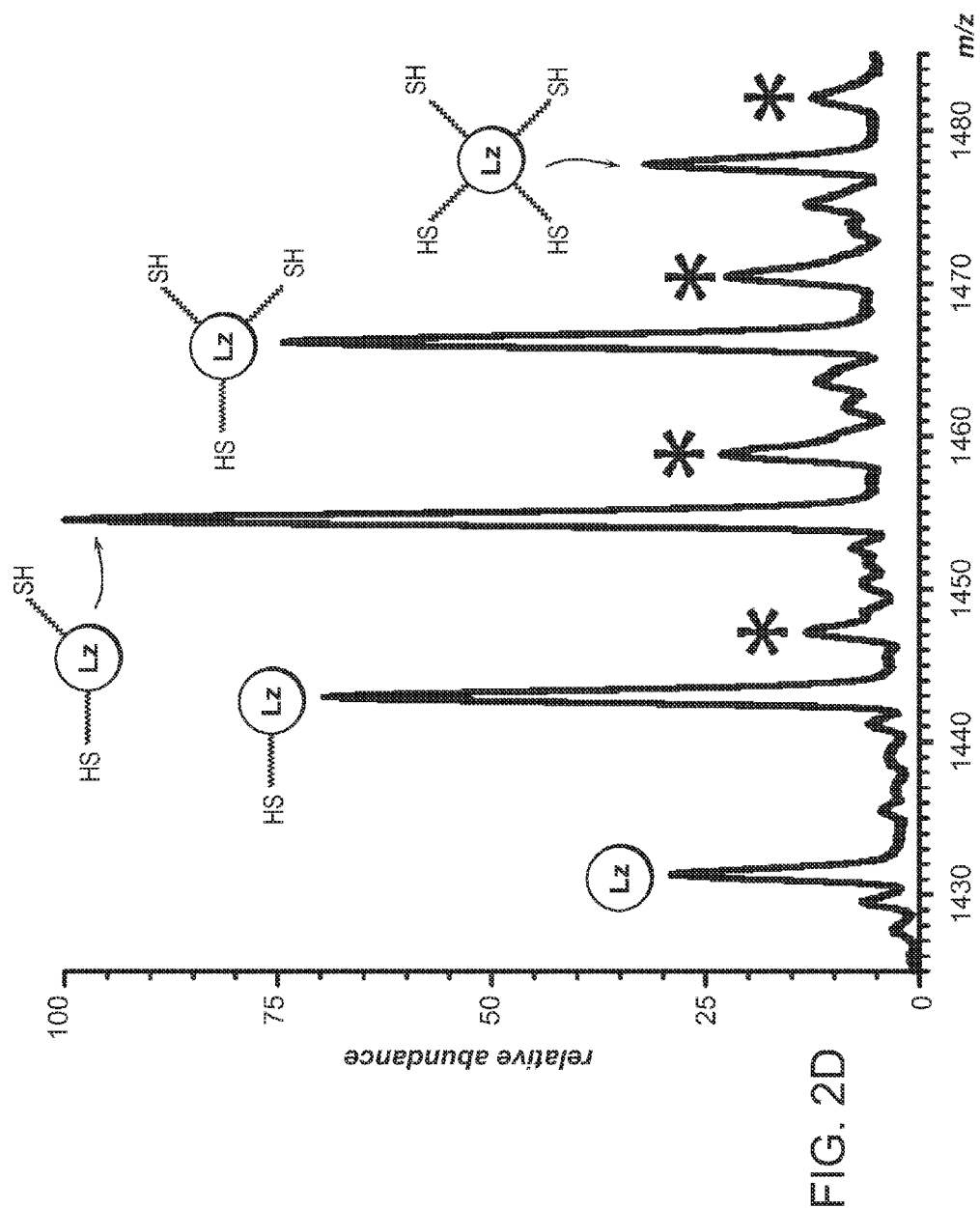
Figure 10:
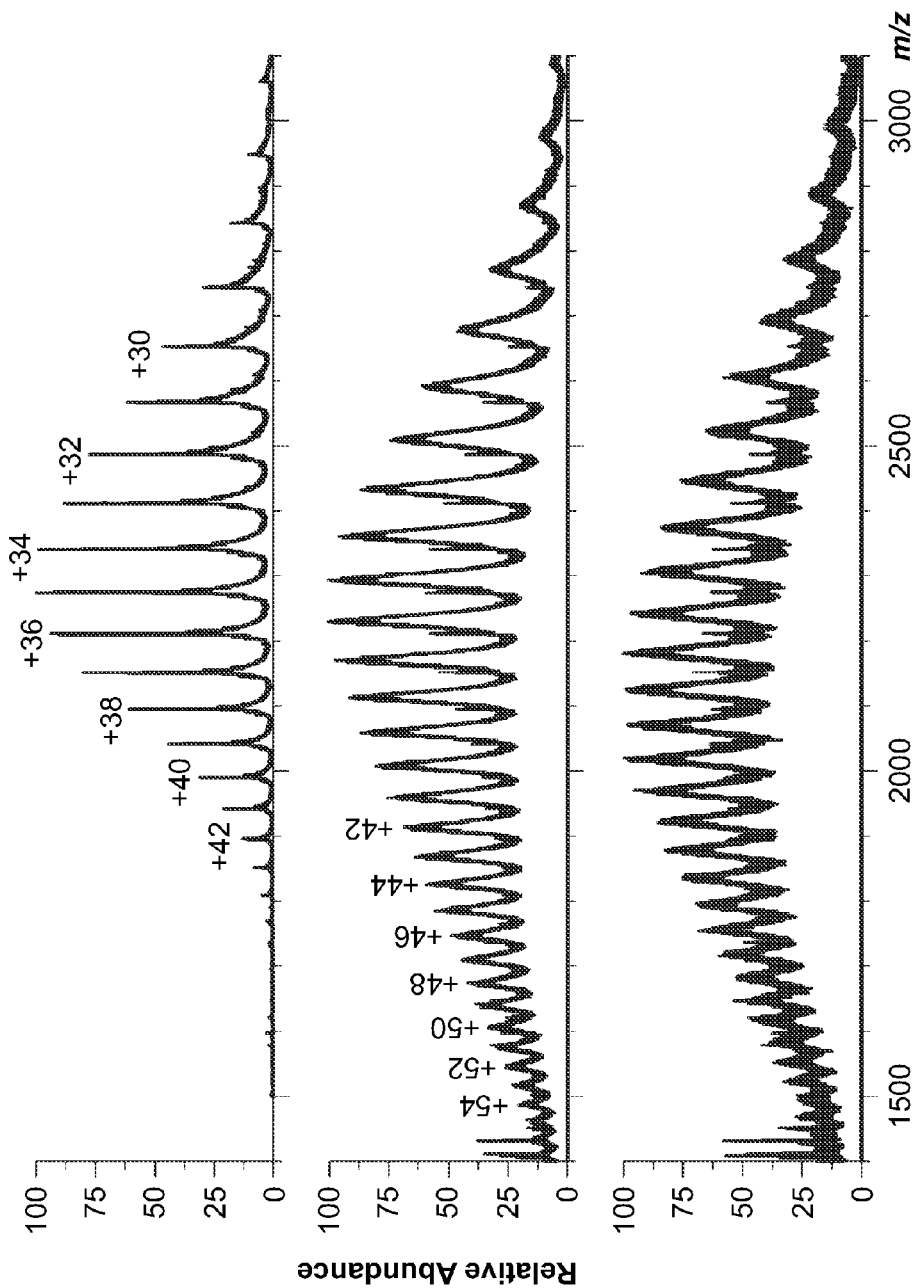
FIG. 10. ESI mass spectra of intact Tf and Tf modified with the Traut's reagent acquired under denaturing conditions. The three traces correspond to an unmodified Tf (top), 1:10 (middle) and 1:20 (bottom) concentration ratio of Tf to Traut's reagent in the reaction. The higher charge state peaks of activated Tf compare to control Tf indicate further unfolding due to the reduction of intramolecular disulfide bonds.
Figure 11:
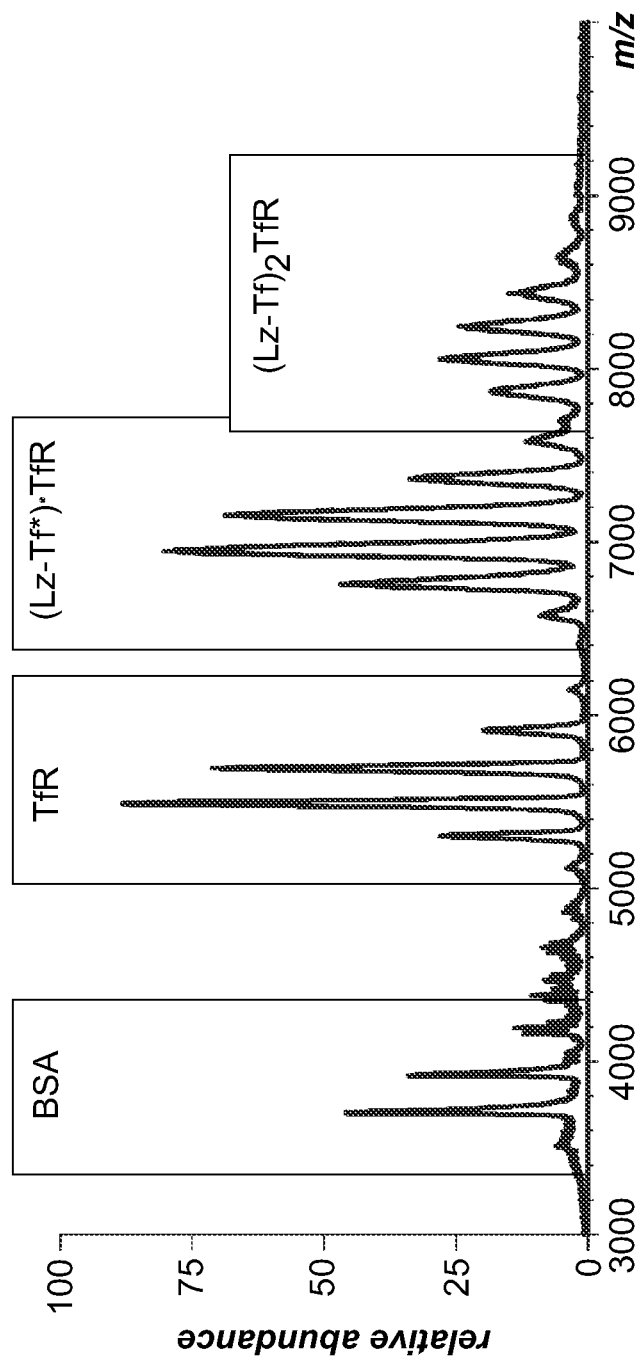
FIG. 11. ESI mass spectrum of a mixture of Lz-Tf conjugate (produced with SM(PEG)12 as a linker) and TfR acquired under near-native conditions. BSA that was present as an impurity in the TfR sample also served as a negative control to ensure specificity of binding for the Lz-Tf conjugate.

Of the two modification reactions, thiolation by Traut's reagent was a challenge. Two aspects addressed were the reduction of intramolecular disulfide bonds and formation of N-substituted 2-iminothilane (NSI) products. The abundance of intramolecular disulfide bonds within Tf was a consideration when this protein was chosen for activation by Traut's reagent. While a high yield of thiolated Tf could be obtained at elevated pH and a high concentration of reagents, the native disulfide bonds of Tf were largely reduced, leading to a changes in its higher order structure (FIG. 10). Disulfide reduction was observed (to a much lesser extent) in the thiolation of Lz by Traut's reagent, but was practically eliminated by reducing reagent concentrations and performing the reaction on ice. In addition to thiolated proteins, other chemical modifications were observed with masses consistent with certain non-thiol byproducts. It is believed these dead-end (non-reactive) products form when the unstable thiol adduct breaks down into a non-reactive 5-membered ring and reduce the number of free thiol groups. Such instability in one of the activating groups can influence downstream conjugation even when all six Lys residues of Lz have been functionalized (FIG. 2B). Formation of NSI by-products was also observed during and after the conjugation reaction, but was minimized by lowering the reaction pH and temperature. We assessed the use of N-succinimidyl S-acetylthioacetate (SATA) as an alternative reagent to introduce the desired thiol group. SATA introduces a "protected sulfhydryl" which involves activation by a mild reducing reagent to expose the sulfhydryl prior to the conjugation reaction. Compared to Traut's reagent, Lz functionalized with SATA had increased stability (did not form NSIs) and reduced heterogeneity (FIG. 2B,D) under the assessed conditions.

Optimizing the activating steps for each protein focused initially on minimizing deleterious or non-productive byproducts such as the reduction of intramolecular disulfide bonds or the formation of NSIs as monitored by ESI MS. After screening pH values from 7.0 to 9.0, reaction temperatures from 0 to 37° C., and reaction times from 0.5 to 24 hours, the optimized thiolation reaction was performed at pH 8, 0° C., for 12 h. Notably, in the examined range of protein concentrations (50 µM to 500 µM), elevated protein concentration was found to result in a higher yield of modified Lz. Different ratios of protein primary amine to reagent from 2:1 to 1:4 were used to generate a series of differentially modified Lz. The optimal extent of Lz activation was determined in conjunction with the optimal extent of Tf activation selecting for values that produced the highest yield of the 1:1 Lz-Tf conjugate. The final conditions for Lz activation utilized an equimolar ratio of primary amine groups relative to activating reagent and introduced 2 to 2.5 thiol groups per Lz. Similar reaction parameters were screened to optimize the activation of Tf with its thiol reactive group. Tf was optimally activated at pH 7.0, 25° C. using 50 µM of Tf and a ratio of Tf to activating reagent of 1:2 for 90 min. Under these conditions, the average number of functional groups incorporated into Tf was 1.5. In the final round of optimization, formation of the Lz-Tf conjugate was monitored as a function of pH, time, temperature as well as the extent of activation of each protein. A high yield of a 1:1 Lz-Tf conjugate was obtained at pH 7 allowing activated Tf and Lz (50 µM each) to react for 12 h at 4° C. Nevertheless, even though ESI MS analysis of the conjugation reaction (FIG. 3A) shows the presence of the 1:1 Lz-Tf conjugate (charge states assigned based on the calculated mass of 94.4 kDa are shown in FIG. 3A with dotted lines), a large number of other species are also present in the mixture. Therefore, various properties of Lz-Tf may be evaluated. It may be advantageous to separate Lz-Tf from other products and/or reagents. Since the incremental mass increase of Lz-Tf over intact Tf makes use of SEC impractical for purification of the conjugation products, alternative methods of separating the 1:1 Lz-Tf conjugate from other components of the reaction mixture were examined.

The significant difference in pI values for Tf (5.5-6.3) and Lz (11.0) made ion exchange chromatography (IXC) particularly attractive as a means of purifying the reaction products. Using a weak cation exchange stationary phase, a mobile phase buffered to pH 6.5, and a shallow salt gradient we have been able to achieve separation between the Tf and Lz peaks exceeding 15 minutes (FIG. 3C), with Lz homopolymers having even longer elution times. The products of the Lz/Tf conjugation reaction elute within a wide (9-17 min) time period and are mostly unresolved, although a distinct peak is observed at 14 min elution time. Collection of a corresponding IXC fraction (13.5-14.5 min) followed by quick desalting and off-line ESI MS analysis yields a mass spectrum consistent with the 1:1 Lz-Tf conjugate as the major component of this fraction (FIG. 3B).

Figure 4A:
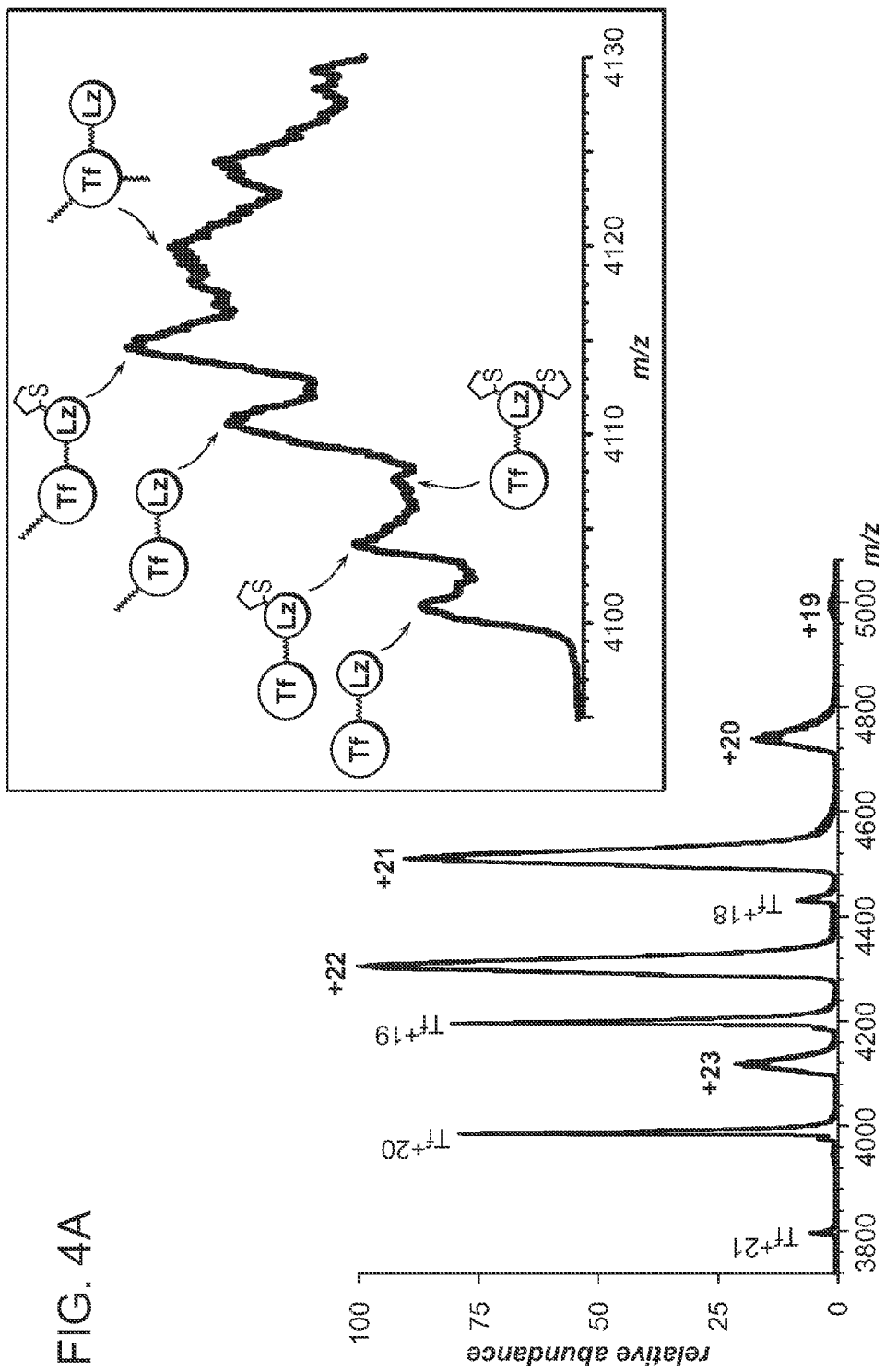
FIGS. 4A-4B. ESI mass spectra of the purified 1:1 Lz-Tf conjugate (short linker) spiked with intact Tf (FIG. 4A) and a 1:1 conjugate produced with a longer linker (FIG. 4B) acquired under near-native conditions (3 µM of each protein in 20 mM ammonium acetate, pH 7.1). Insets zoom in on a selected charge state for each of the conjugates.
Figure 4B:
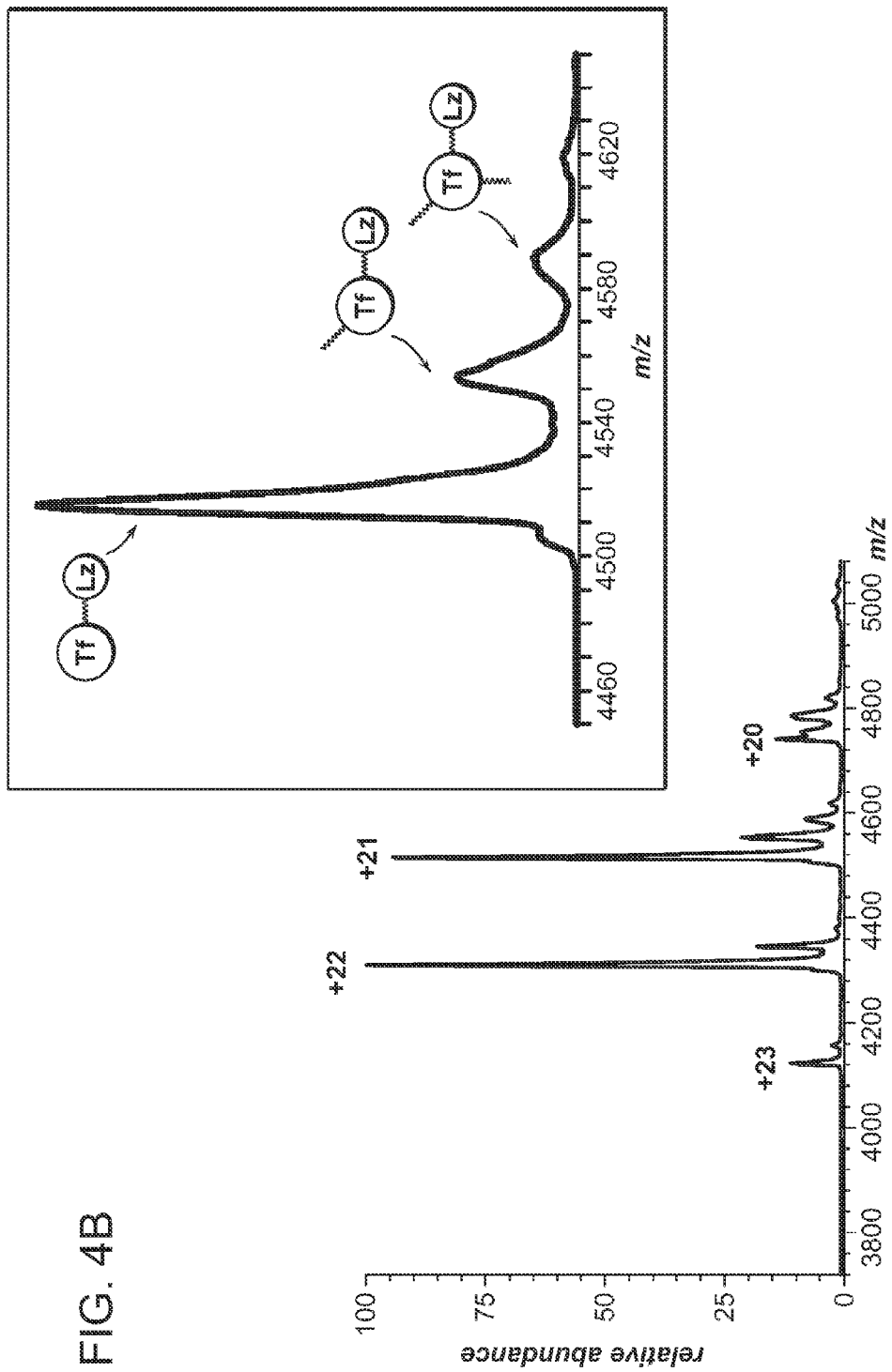

Even though the collected IXC fraction represents a 1:1 Lz-Tf conjugate, there still might be a significant degree of micro-heterogeneity due to the presence of modified Lys side chains on the surfaces of both Tf and Lz. Indeed, native ESI MS analysis of this fraction spiked with intact Tf (FIG. 4) shows significantly broader peak shapes for multiply charged Lz-Tf ions compared to intact Tf ions. An analysis of the mass spectrum reveals convoluted peak shapes for Lz-Tf ions (insets in FIG. 4), where the ionic mass distribution is due to the presence of either unreacted maleimide groups on the surface of Tf and/or dead-end NSI groups on the surface of Lz. No large scale conformational changes were apparent as a result of the conjugation reaction, as the charge state distribution of Lz-Tf ions is consistent with both components of the conjugate maintaining compact structures in solution (no ions were detected in the low m/z region, whose presence in ESI MS usually signals either partial or complete protein unfolding in solution).

Example 3: Influence of Conjugation and Chemical Modifications on Interaction with Transferrin Receptor (TfR)

Examination of the Lz-Tf conjugate with native ESI MS indicated that neither protein undergoes unfolding as a result of the conjugation. We evaluated the ability of both Tf and Lz to interact with their physiological partners and/or therapeutic targets.

Figure 5:
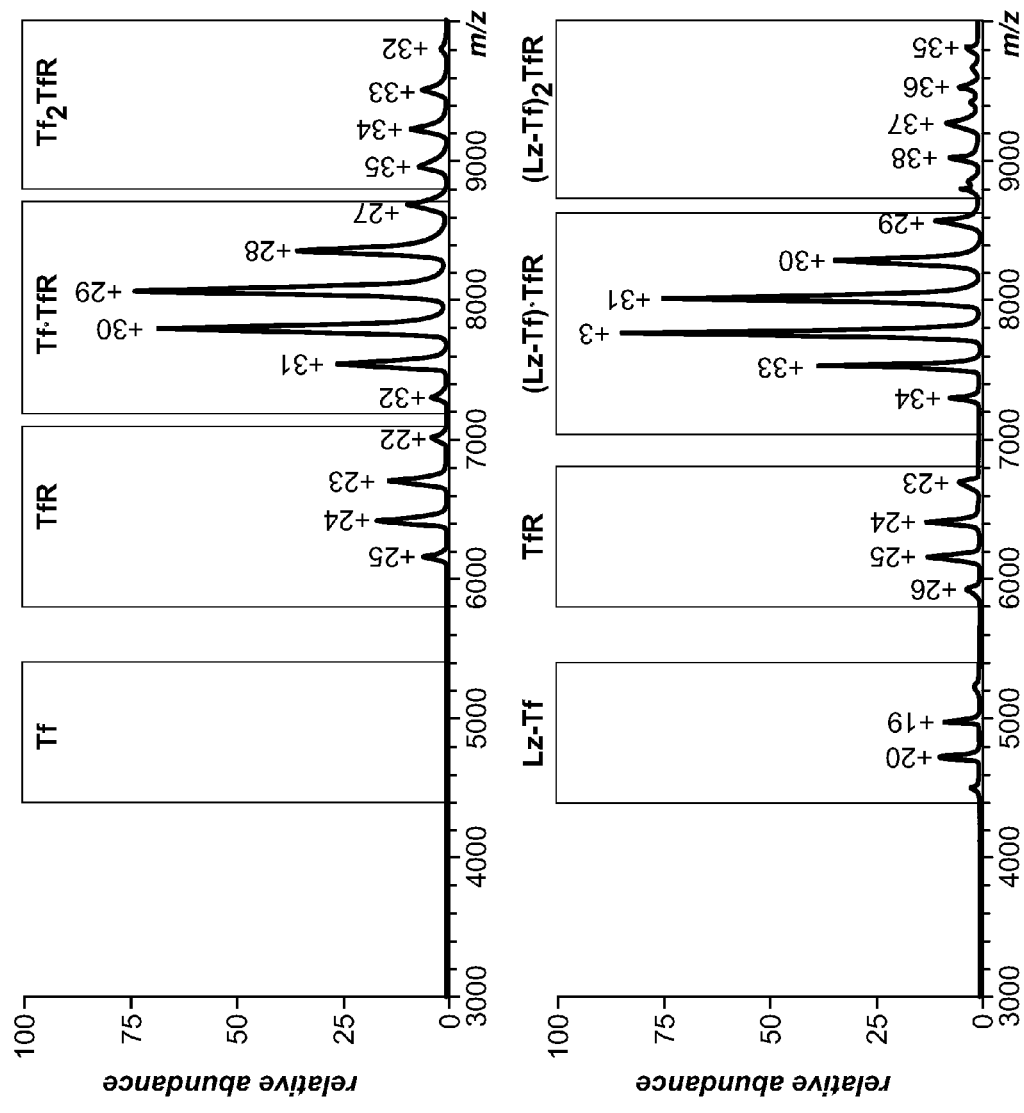
FIG. 5. ESI mass spectra of Tf/TfR (top) and Lz-Tf/TfR (bottom) mixtures acquired under near-native conditions (3 µM of each protein in 20 mM ammonium acetate, pH 7.1).

Native ESI MS provides a method to evaluate protein binding to a variety of ligands, including both small molecules and biopolymers, and in some instances allows the binding affinity to be estimated. This approach is useful for monitoring TfR (Transferring receptor) recognition by wild type Tf and its mutants under a variety of conditions, and for monitoring interactions of a Tf-based fusion protein with TfR. An ESI mass spectrum of the Lz-Tf/TfR mixture acquired in this work under near native conditions (neutral pH, ionic strength 20 mM) indicates that the receptor does recognize the conjugate (FIG. 5). Indeed, no ionic signal of unbound $Fe_2Tf$ is detected in the mass spectrum of the $Fe_2Tf/TfR$ mixture, consistent with the receptor-binding affinity of $Fe_2Tf$ being in the sub-µM range (concentration of both proteins in the $Fe_2Tf/TfR$ mixture was in the low-µM range, 3 µM). At the same time, the presence of a weak, but detectable ionic signal of unbound Lz-Tf in the mass spectrum of the Lz-Tf/TfR mixture acquired under identical conditions suggests that the TfR binding affinity of the conjugate is in the low-µM range. This affinity range is close to that of intact apo-Tf, even though the conjugate was saturated with iron following its isolation from the reaction mixture and its measured mass is in agreement with the diferric form. This lower receptor affinity is sufficient for transient binding to TfR at the cell surface (endogenous Tf is only 30% saturated with iron), and may advantageous for dissociation from TfR upon crossing the BBB.

Figure 6A:
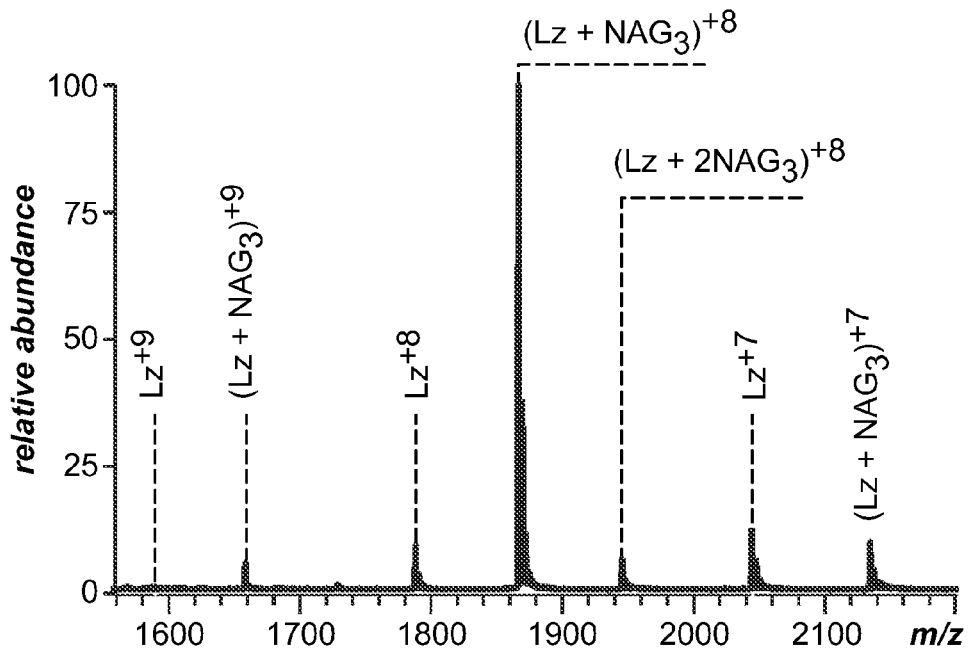
Figure 6B:
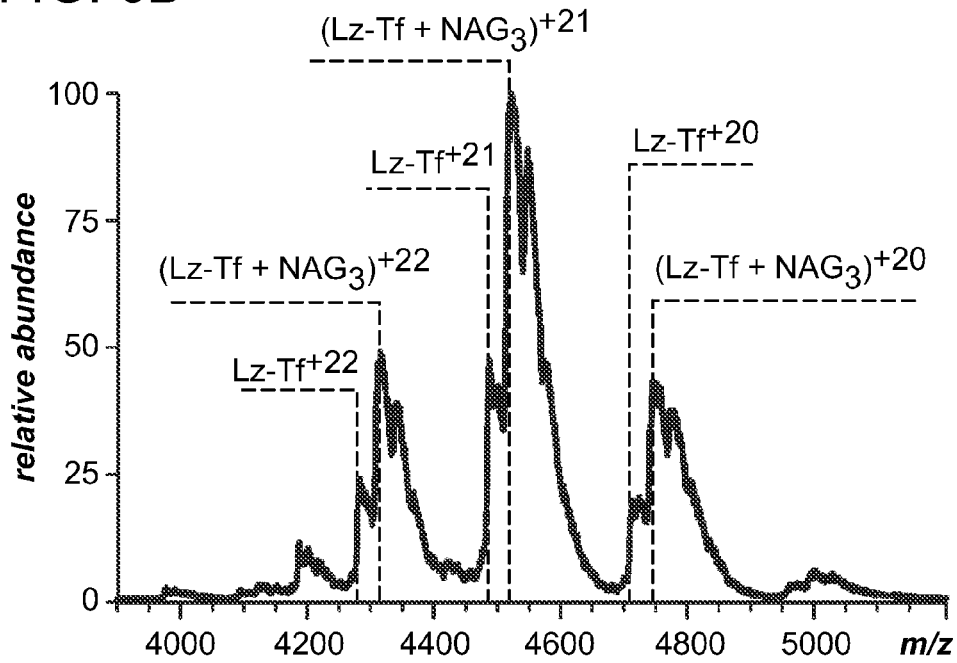

Example 4: Influence of Conjugation and Chemical Modification on Enzymatic Activity In order to exhibit bacteriostatic properties, enzymatic activity of Lz must be preserved within the conjugate. Enzymatic activity of Lz and its variants is frequently probed using the short tri-saccharide $NAG_3$ as a surrogate substrate to demonstrate the substrate-binding competence of the protein (FIG. 6A). Lz-Tf retains the ability to bind $NAG_3$, indicated by the presence of the protein-$NAG_3$ complexes in the mass spectrum of a Lz-Tf/$NAG_3$ mixture (FIG. 6B) acquired under near-native conditions (neutral pH and 20 mM ionic strength), a behavior very similar to that exhibited by intact Lz.

Substrate binding results obtained using $NAG_3$ were promising. A photometric-based activity assay that measures the lysis of Gram-positive bacteria indicated a very significant loss of bacteriolytic activity by Lz-Tf (FIG. 7). As can be seen in Table 1, the bacteriolytic activity of Lz-Tf compared to the control (intact) Lz. Bacteriolytic activity of the Lz dimer was also assessed (See Table 1) after adjusting it by a factor of 2 due to the presence of two catalytic sites in a single $Lz_2$ molecule. It was determined that differences in the ability of Lz-Tf to catalyze the hydrolysis of large glycans compared with control Lz may be associated with steric restraints introduced by a bulky "anchor" (Tf).

This effect may be controlled by the use of different linkers (e.g., longer linkers), which increase the freedom of movement of Lz cross-linked to Tf, allowing it to attack the bacterial cell walls more effectively. For example, protein/protein conjugate with a longer linkers is provided by amine-reactive $SM(PEG)_{12}$, which also introduces a thiol-reactive maleimide group on the protein surface (FIG. 1C). Activation of Tf with this reagent and introduction of free thiol groups to Lz using, SATA (to avoid formation of dead-ended by-products introduced by the Traut's reagent, see FIGS. 2 B and D) leads to formation of a conjugate that is recognized by TfR (see FIG. 10) and has anti-bacterial activity over an order of magnitude higher than that of the conjugate with a short linker (FIG. 7). Although a fraction of that increase may be associated with using SATA as the enzyme-modifying reagent (note that the covalent dimer of SATA-modified Lz retains half the activity of the intact enzyme, see Table 1), a significant gain is a result of using the longer (and more flexible) linker.

Example 5: Stability Evaluation of Transferrin-Lysozyme Conjugate

In addition to demonstrated biological activity and a favorable pharmacokinetic profile, a desirable feature of a protein-based drug is superior stability characteristics, including resistance to the formation of protein aggregates. Protein aggregates result not only in a loss of therapeutic efficacy, but also have the potential to trigger the immune response of the host organism, thereby raising safety concerns. Therefore, the stability of the transferrin-lysozyme (Lz-Tf) conjugate was evaluated both prior to administration (during a prolonged storage) and post-administration (in vivo).

The aggregation propensity of a Lz-Tf conjugate was evaluated using size-exclusion chromatography (SEC) with on-line spectrophotometric and/or off-line inductively coupled plasma mass spectrometric (ICP MS) detection. A SEC chromatogram of freshly prepared Lz-Tf in 150 mM $CH_3CO_2NH_4$ shows a single peak whose elution time corresponds to the monomeric form of the conjugate (FIG. 12 A), and is closely mirrored by the chromatogram of the conjugate that was lyophilized and stored at −20° C. for one month prior to reconstitution in 150 mM $CH_3CO_2NH_4$ for SEC analysis (FIG. 12C). The presence of the monomer-associated peaks in both samples indicated that long term storage does not affect the aggregation propensity of the Lz-Tf conjugate. Instability of the Lz-Tf conjugate was seen, however, when it was exposed to increased temperature for a prolonged period of time. Incubating the Lz-Tf conjugate in an aqueous solution for 24 hours at 37° C. in vitro produced low levels of protein aggregates, as indicated by the appearance of peaks at short elution time (<9 min.) in SEC chromatogram (FIG. 12 B). However, in vivo evaluation, carried out by spiking mouse serum with Lz-Tf and analyzing the protein complement of the serum with SEC following a 24-hour incubation at 37° C. did not provide any signs of the aggregation onset in the Lz-Tf-spiked serum when compared to the untreated control (FIG. 12 D).

In order to maintain the desired activity, the conformational integrity of the Lz-Tf monomer should be preserved in vivo. Therefore, the effects of storage conditions on the in vivo conformational integrity of monomeric Lz-Tf SEC fractions were tested by native ESI MS (FIG. 13). Previous analysis of freshly prepared samples indicates that the Lz-Tf conjugate maintains a compact, folded structure in an aqueous solution (as seen in Example 2). The chromatograms represented in FIG. 13 show that neither the Lz-Tf sample stored for one month in the lyophilized form (FIG. 13 A) nor the monomer retrieved from the sample kept in aqueous solution for one day at room temperature (FIG. 13 B) show any signs of complete or partial unfolding (which manifests itself in native ESI MS via the appearance of high charge density ionic species, such as those shown in (FIG. 13 C) for the conjugate exposed to 0.1% of formic acid (FA)).

In summary, a suite of ESI MS-based methods has been applied to characterize the structural and conformational integrity of a model bacteriostatic agent (Lz) conjugated to a transport protein (Tf), as well as its interaction with a physiological partner (TfR) important for delivery of this product to the CNS. Interaction of Lz-Tf with therapeutic targets was evaluated initially using ESI MS to monitor binding to a small surrogate substrate (NAG3) followed by measuring its bacteriolytic activity, and comparing its level to that of the intact Lz and Lz dimer. These indicate that in some embodiments steric hindrance imposed by a large protein anchored closely to the Lz surface may affect its biological activity. Increasing the autonomy of Lz by lengthening the linker led to a dramatic increase in the bacteriolytic activity of the conjugate. ESI MS is a tool facilitating the protein drug development process, and this work demonstrates the effectiveness of this technique as a means to facilitate development of a range of therapeutically effective protein-drug conjugates.

Overcoming the neuroanatomical obstacle for delivery of Lz to the CNS (the blood-brain barrier, BBB) is addressed by chemically conjugating this protein to transferrin (Tf). Tf is a carrier that the therapeutic protein uses to target tissues via transferrin receptor (TfR) mediated endocytosis and/or across physiological barriers (such as the intestinal epithelial barrier) via TfR mediated transcytosis. The conjugate may be produced by activating Lz using N-succinimidyl-S-acetylthioacetate (SATA), which places free thiol groups on lysine side chains and incorporating thiol-reactive maleimide groups into human Tf using succinimidyl-([N-maleimidopropionamido]-dodecaethyleneglycol) ester (SM $(PEG)_{12}$). A non-cleavable thio-ether linkage between activated Lz and Tf is formed by incubating a mixture of the two modified proteins, and the 1:1 Lz-Tf conjugate may be isolated using cation exchange chromatography.

Examination of the Lz-Tf conjugate with electrospray ionization mass spectrometry (ESI MS) suggests that neither protein component undergoes unfolding as a result of conjugation (the charge state distribution of Lz-Tf ions in ESI MS is consistent with both components of the conjugate maintaining compact structures in solution, see the attached manuscript for more detail).

Bacteriostatic properties of the conjugate were examined by (i) monitoring its ability to recognize a short tri-saccharide NAG3, which frequently serves as a surrogate substrate to demonstrate the substrate-binding competence of Lz, and (ii) measuring the lysis kinetics of Gram-positive *Micrococcus lysodeikticus*. Both methods indicate that the bacteriolytic activity of lysozyme is present within the conjugate. This work showing Lz as a payload targeted to the CNS, is relevant to other bacteriostatic agents, which have antimicrobial properties, but cannot cross the BBB without being assisted by a transport protein.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, and/or method described herein. In addition, any combination of two or more such features, systems, articles, materials, and/or methods, if such features, systems, articles, materials, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

Use of ordinal terms such as "first," "second," "third," etc., in the claims to modify a claim element does not by itself connote any priority, precedence, or order of one claim element over another or the temporal order in which acts of a method are performed, but are used merely as labels to distinguish one claim element having a certain name from another element having a same name (but for use of the ordinal term) to distinguish the claim elements.

What is claimed is:

1. A compound of the formula:

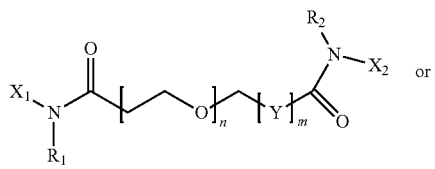 or 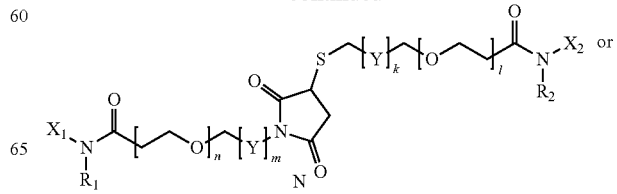

-continued $$X_1 \diagdown \underset{R_1}{N} \diagdown \overset{O}{\underset{}{\|}} \diagdown [\diagdown O \diagdown]_n [Y]_m \diagdown N(\text{succinimide}) \diagdown S \diagdown C(=O) \diagdown N(R_2) \diagdown X_2$$

where $X_1$ is a transferrin receptor ligands, $X_2$ is a glycoside hydrolase, and wherein n and l are each independently an integer from 1 to 100, wherein m and k are each independently an integer from 1 to 4, wherein each instance of Y is independently selected from the group consisting of —N(R$_3$)C(=O)—, —C(=O)N(R$_3$)—, and —C(R$_4$)$_2$—, and wherein:

$R_1$, $R_2$, and each instance of $R_3$ are independently selected from the group consisting of hydrogen, C1-6 alkyl, and a nitrogen protecting group;

each instance of $R_4$ is independently selected from the group consisting of a hydrogen, halogen, acyl, alkyl, alkenyl, alkynyl, carbocyclyl, heterocyclyl, aryl, heteroaryl, —OR$_A$, —N(R$_A$)$_2$, —SR$_A$, —CN, —SCN, —C(=NR$_A$)R$_A$, —C(=NR$_A$)OR$_A$, —C(=NR$_A$)N(R$_A$)$_2$, —C(=O)R$_A$, —C(=O)OR$_A$, —C(=O)N(R$_A$)$_2$, —NO$_2$, —NR$_A$C(=O)R$_A$, —NR$_A$C(=O)OR$_A$, —NR$_A$C(=O)N(R$_A$)$_2$, —OC(=O)R$_A$, —OC(=O)OR$_A$, —OC(=O)N(R$_A$)$_2$, and a nitrogen protecting group when attached to a nitrogen atom, or two $R_A$ groups are joined to form a carbocyclic, heterocyclic, aryl, or heteroaryl ring; and each instance of $R_A$ is independently selected from the group consisting of a hydrogen, acyl, alkyl, alkenyl, alkynyl, carbocyclyl, heterocyclyl, aryl, heteroaryl, a nitrogen protecting group when attached to a nitrogen atom, an oxygen protecting group when attached to an oxygen atom, and a sulfur protecting group when attached to a sulfur atom, or two $R_A$ groups are joined to form a heterocyclic ring.

2. The compound of claim 1, which is of the formula:

$$X_1 \diagdown \underset{R_1}{N} \diagdown \overset{O}{\|} \diagdown [\diagdown O \diagdown]_n [Y]_m \diagdown N(\text{succinimide}) \diagdown S \diagdown C(=O) \diagdown N(R_2) \diagdown X_2.$$

3. The compound of claim 1, wherein the transferrin receptor ligand is transferrin.

4. The compound of claim 3, where the transferrin is a human transferrin.

5. The compound of claim 1, wherein the transferrin receptor ligand is an antibody or antigen-binding fragment that selectively binds to the transferrin receptor.

6. The compound of claim 1, wherein the glycoside hydrolase is a lysozyme.

7. The compound of claim 6, wherein the lysozyme is a human lysozyme.

8. The compound of claim 1, wherein the glycoside hydrolase hydrolyzes the β-1,4-glycosidic bond between the N-acetylmuramic acid (NAM) and N-acetylglucosamine (NAG) residues of peptidoglycans.

9. The compound of claim 1, wherein the glycoside hydrolase hydrolyzes the 1,4-beta-linkages between N-acetyl-D-glucosamine residues in chitodextrins.

10. A compound of the formula:

$$X_1 \diagdown \underset{R_1}{N} \diagdown \overset{O}{\|} \diagdown [\diagdown O \diagdown]_n \diagdown NH \diagdown C(=O) \diagdown N(\text{succinimide}) \diagdown S \diagdown C(=O) \diagdown N(R_2) \diagdown X_2$$

wherein $X_1$ is a transferrin receptor ligand, and $X_2$ is a glycoside hydrolase.

11. A compound of the formula $$Tf \diagdown NH \diagdown C(=O) \diagdown [\diagdown O \diagdown]_n \diagdown NH \diagdown C(=O) \diagdown N(\text{succinimide}) \diagdown S \diagdown C(=O) \diagdown NH \diagdown Lz,$$

wherein Tf is transferrin and Lz is lysozyme.

12. A multimeric compound comprising a plurality of covalently linked monomers of the formula as set forth in claim 1.

13. A composition comprising a plurality of compounds, each of which compounds has a formula as set forth in claim 1.

14. A method of killing gram-positive bacteria, the method comprising contacting the bacteria with a compound of claim 1 in an amount effective to breakdown the cell wall of the bacteria, thereby killing the bacteria.

15. A method of treating a bacterial infection of the central nervous system (CNS) in a subject, the method comprising administering to the CNS of the subject the composition of claim 13 in an amount effective for treating a bacterial infection in the CNS.

16. The method of claim 15 wherein the step of administering comprising delivering the composition to the subject intravenously, wherein the compound enters the CNS by crossing the blood-brain-barrier.

17. The method of claim 15 further comprising determining that the bacterial infection caused by a gram-positive bacteria, prior to administering the composition to the subject.

18. The method of claim 17 further comprising obtaining a sample of CNS fluid from the subject and performing an assay to detect the presence of gram-positive bacteria in the CNS fluid.

19. The method of claim 18, wherein the assay is a Gram stain assay or PCR assay.

* * * * *